(12) United States Patent
Muller

(10) Patent No.: US 10,105,475 B2
(45) Date of Patent: Oct. 23, 2018

(54) CATHETER PUMP INTRODUCER SYSTEMS AND METHODS

(71) Applicant: TC1 LLC, St. Paul, MN (US)

(72) Inventor: Paul F. Muller, San Carlos, CA (US)

(73) Assignee: TC1 LLC, Pleasanton, CA (US)

( * ) Notice: Subject to any disclaimer, the term of this patent is extended or adjusted under 35 U.S.C. 154(b) by 0 days.

(21) Appl. No.: 15/303,709

(22) PCT Filed: Apr. 15, 2015

(86) PCT No.: PCT/US2015/026025
§ 371 (c)(1),
(2) Date: Oct. 12, 2016

(87) PCT Pub. No.: WO2015/160990
PCT Pub. Date: Oct. 22, 2015

(65) Prior Publication Data
US 2017/0035952 A1   Feb. 9, 2017

Related U.S. Application Data

(60) Provisional application No. 61/979,937, filed on Apr. 15, 2014.

(51) Int. Cl.
*A61M 1/10* (2006.01)
*A61M 1/12* (2006.01)

(52) U.S. Cl.
CPC ........ *A61M 1/1024* (2014.02); *A61M 1/1008* (2014.02); *A61M 1/101* (2013.01);
(Continued)

(58) Field of Classification Search
CPC .............. A61M 1/1024; A61M 1/1008; A61M 1/1034; A61M 1/1082; A61M 1/1084; A61M 1/122; A61M 1/125; A61M 1/101
See application file for complete search history.

(56) References Cited

U.S. PATENT DOCUMENTS

| 1,902,418 | A | 3/1933 | Pilgrim |
| 2,356,659 | A | 10/1942 | Aguiar |

(Continued)

FOREIGN PATENT DOCUMENTS

| CA | 2701810 | 4/2009 |
| EP | 0 533 432 | 9/1992 |

(Continued)

OTHER PUBLICATIONS

Abiomed, "Impella 5.0 with the Impella Console, Circulatory Support System, Instructions for Use & Clinical Reference Manual," Jun. 2010, in 122 pages.

(Continued)

*Primary Examiner* — Scott Getzow
(74) *Attorney, Agent, or Firm* — Armstrong Teasdale LLP

(57) ABSTRACT

A catheter system for a catheter pump is disclosed. The system can include an elongate catheter body having a distal portion including an expandable cannula having an inlet and an outlet. The expandable cannula can have a delivery profile and an operational profile larger than the delivery profile. An impeller assembly can include an impeller shaft and an impeller body. A sheath can have a cannula retention zone disposed over the expandable cannula and a separation zone. The cannula retention zone can have a first configuration adapted to retain the expandable cannula in the delivery profile. The system can be adapted to separate the separation zone into a first portion and a second portion disposed across a gap. The gap can enable the elongate catheter body to pass between the first and second portion so that the sheath can be removed from the elongate catheter body.

18 Claims, 14 Drawing Sheets

(52) U.S. Cl.
CPC ......... *A61M 1/1034* (2014.02); *A61M 1/1082* (2014.02); *A61M 1/1084* (2014.02); *A61M 1/122* (2014.02); *A61M 1/125* (2014.02)

(56) References Cited

U.S. PATENT DOCUMENTS

| | | | |
|---|---|---|---|
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Donaldson |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Volder |
| 4,304,524 A | 12/1981 | Coxon et al. |
| 4,382,199 A | 5/1983 | Isaacson |
| 4,392,836 A | 7/1983 | Sugawara |
| 4,458,366 A | 7/1984 | MacGregor |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,686,982 A | 8/1987 | Nash |
| 4,696,667 A | 9/1987 | Masch |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffman et al. |
| 5,021,048 A | 6/1991 | Buckholtz |
| 5,045,072 A | 9/1991 | Castillo et al. |
| 5,049,134 A | 9/1991 | Golding et al. |
| 5,061,256 A | 10/1991 | Wampler |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,147,186 A | 9/1992 | Buckholtz |
| 5,163,910 A | 11/1992 | Schwartz et al. |
| 5,169,378 A | 12/1992 | Figuera |
| 5,171,212 A | 12/1992 | Buck et al. |
| 5,190,528 A | 3/1993 | Fonger et al. |
| 5,195,960 A | 3/1993 | Hossain et al. |
| 5,201,679 A | 4/1993 | Velte et al. |
| 5,211,546 A | 5/1993 | Isaacson et al. |
| 5,221,270 A | 6/1993 | Parker |
| 5,234,407 A | 8/1993 | Teirstein et al. |
| 5,234,416 A | 8/1993 | Macaulay et al. |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,376,114 A | 12/1994 | Jarvik |
| 5,393,197 A | 2/1995 | Lemont et al. |
| 5,393,207 A | 2/1995 | Maher et al. |
| 5,405,341 A | 4/1995 | Martin |
| 5,405,383 A | 4/1995 | Barr |
| 5,415,637 A | 5/1995 | Khosravi |
| 5,437,541 A | 8/1995 | Vainrub et al. |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,534,287 A | 7/1996 | Lukic |
| 5,554,114 A | 9/1996 | Wallace et al. |
| 5,588,812 A | 12/1996 | Taylor et al. |
| 5,609,574 A | 3/1997 | Kaplan et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman et al. |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio, III et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,776,161 A | 7/1998 | Globerman |
| 5,776,190 A | 7/1998 | Jarvik |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,859,482 A | 1/1999 | Crowell et al. |
| 5,868,702 A | 2/1999 | Stevens |
| 5,868,703 A | 2/1999 | Bertolero |
| 5,888,241 A | 3/1999 | Jarvik |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio, III et al. |
| 6,053,705 A | 4/2000 | Schob et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |

(56) References Cited

U.S. PATENT DOCUMENTS

| | | |
|---|---|---|
| 6,086,527 A | 7/2000 | Talpade |
| 6,086,570 A | 7/2000 | Aboul-Hosn et al. |
| 6,106,494 A | 8/2000 | Saravia et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,190,357 B1 | 2/2001 | Ferrari et al. |
| 6,200,260 B1 | 3/2001 | Bolling |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,454,775 B1 | 9/2002 | Demarais et al. |
| 6,468,298 B1 | 10/2002 | Pelton |
| 6,503,224 B1 | 1/2003 | Forman et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 * | 3/2003 | Schmitz-Rode .......... F04D 3/02 600/16 |
| 6,544,216 B1 | 4/2003 | Sammler et al. |
| 6,547,519 B2 | 4/2003 | de Blanc et al. |
| 6,565,598 B1 | 5/2003 | Lootz |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,652,548 B2 | 11/2003 | Evans et al. |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Grundeman et al. |
| 6,794,784 B2 | 9/2004 | Takahashi et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,818,001 B2 | 11/2004 | Wulfman et al. |
| 6,860,713 B2 | 3/2005 | Hoover |
| 6,866,625 B1 | 3/2005 | Avre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,229,258 B2 | 6/2007 | Wood et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Keren et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,469,716 B2 | 12/2008 | Parrino et al. |
| 7,491,163 B2 | 2/2009 | Viole et al. |
| 7,534,258 B2 | 5/2009 | Gomez |
| 7,605,298 B2 | 10/2009 | Bechert et al. |
| 7,619,560 B2 | 11/2009 | Penna |
| 7,633,193 B2 | 12/2009 | Masoudipour et al. |
| 7,645,225 B2 | 1/2010 | Medvedev et al. |
| 7,657,324 B2 | 2/2010 | Westlund et al. |
| 7,682,673 B2 | 3/2010 | Houston et al. |
| 7,722,568 B2 | 5/2010 | Lenker et al. |
| 7,731,675 B2 | 6/2010 | Aboul-Hosn et al. |
| 7,736,296 B2 | 6/2010 | Siess et al. |
| 7,758,521 B2 * | 7/2010 | Morris ............ A61B 17/00234 600/585 |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |
| 7,828,710 B2 | 11/2010 | Shifflette |
| 7,841,976 B2 | 11/2010 | McBride et al. |
| 7,878,967 B1 | 2/2011 | Khanal |
| 7,918,828 B2 | 4/2011 | Lundgaard et al. |
| 7,927,068 B2 | 4/2011 | McBride et al. |
| 7,935,102 B2 | 5/2011 | Breznock et al. |
| 7,942,804 B2 | 5/2011 | Khaw |

(56) References Cited

U.S. PATENT DOCUMENTS

| | | |
|---|---|---|
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 7,998,190 B2 | 8/2011 | Gharib et al. |
| 8,012,079 B2 | 9/2011 | Delgado |
| 8,025,647 B2 | 9/2011 | Siess et al. |
| 8,079,948 B2 | 12/2011 | Shifflette |
| 8,110,267 B2 | 2/2012 | Houston et al. |
| 8,114,008 B2 | 2/2012 | Hidaka et al. |
| 8,123,669 B2 | 2/2012 | Siess et al. |
| 8,177,703 B2 | 5/2012 | Smith et al. |
| 8,206,350 B2 | 6/2012 | Mann et al. |
| 8,209,015 B2 | 6/2012 | Glenn |
| 8,216,122 B2 | 7/2012 | Kung |
| 8,235,943 B2 | 8/2012 | Breznock et al. |
| 8,236,040 B2 | 8/2012 | Mayberry et al. |
| 8,236,044 B2 | 8/2012 | Robaina |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,333,687 B2 | 12/2012 | Farnan et al. |
| 8,348,991 B2 | 1/2013 | Weber et al. |
| 8,364,278 B2 | 1/2013 | Pianca et al. |
| 8,376,707 B2 | 2/2013 | McBride et al. |
| 8,382,818 B2 | 2/2013 | Davis et al. |
| 8,388,565 B2 | 3/2013 | Shifflette |
| 8,409,128 B2 | 4/2013 | Ferrari |
| 8,414,645 B2 | 4/2013 | Dwork et al. |
| 8,439,859 B2 | 5/2013 | Pfeffer et al. |
| 8,449,443 B2 | 5/2013 | Rodefeld |
| 8,485,961 B2 | 7/2013 | Campbell et al. |
| 8,489,190 B2 | 7/2013 | Pfeffer et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan |
| 8,585,572 B2 | 11/2013 | Mehmanesh |
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | LaRose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,634 B2 | 7/2015 | Schumacher et al. |
| 9,089,670 B2 | 7/2015 | Scheckel |
| 9,162,017 B2 | 10/2015 | Evans et al. |
| 9,217,442 B2 | 12/2015 | Wiessler et al. |
| 9,308,302 B2 | 4/2016 | Zeng |
| 9,314,558 B2 | 4/2016 | Er |
| 9,327,067 B2 | 5/2016 | Zeng et al. |
| 9,328,741 B2 | 5/2016 | Liebing |
| 9,358,330 B2 | 6/2016 | Schumacher |
| 2002/0107506 A1 | 8/2002 | McGuckin, Jr. et al. |
| 2003/0018380 A1 | 1/2003 | Craig et al. |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2005/0049696 A1 | 3/2005 | Siess et al. |
| 2005/0085683 A1 | 4/2005 | Bolling et al. |
| 2005/0113631 A1 | 5/2005 | Bolling et al. |
| 2005/0137680 A1 | 6/2005 | Ortiz et al. |
| 2005/0165269 A9 | 7/2005 | Aboul-Hosn et al. |
| 2005/0250975 A1 | 11/2005 | Carrier et al. |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2008/0004645 A1 | 1/2008 | To et al. |
| 2008/0103442 A1 | 5/2008 | Kesten et al. |
| 2008/0103516 A1 | 5/2008 | Wulfman et al. |
| 2008/0119943 A1 | 5/2008 | Armstrong et al. |
| 2008/0132748 A1 | 6/2008 | Shifflete |
| 2008/0167679 A1 | 7/2008 | Papp |
| 2008/0275290 A1 | 11/2008 | Viole et al. |
| 2009/0018567 A1 | 1/2009 | Escudero et al. |
| 2009/0024085 A1 | 1/2009 | To et al. |
| 2009/0099638 A1 | 4/2009 | Grewe |
| 2009/0112312 A1 | 4/2009 | LaRose et al. |
| 2009/0118567 A1 | 5/2009 | Siess |
| 2009/0182188 A1 | 7/2009 | Marseille et al. |
| 2009/0234378 A1 | 9/2009 | Escudero et al. |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0127871 A1 | 5/2010 | Pontin |
| 2010/0210895 A1 | 8/2010 | Aboul-Hosn et al. |
| 2010/0268017 A1 | 10/2010 | Siess |
| 2010/0274330 A1 | 10/2010 | Burwell et al. |
| 2010/0286791 A1 | 11/2010 | Goldsmith |
| 2011/0071338 A1 | 3/2011 | McBride et al. |
| 2011/0076439 A1 | 3/2011 | Zeilon |
| 2011/0152906 A1 | 6/2011 | Escudero et al. |
| 2011/0152907 A1 | 6/2011 | Escudero et al. |
| 2011/0237863 A1 | 9/2011 | Ricci et al. |
| 2012/0004495 A1 | 1/2012 | Bolling |
| 2012/0029265 A1 | 2/2012 | LaRose et al. |
| 2012/0059213 A1 | 3/2012 | Spence |
| 2012/0083740 A1* | 4/2012 | Chebator .......... A61M 25/0074 604/164.03 |
| 2012/0142994 A1 | 6/2012 | Toellner |
| 2012/0172654 A1 | 7/2012 | Bates |
| 2012/0178986 A1 | 7/2012 | Campbell et al. |
| 2012/0184803 A1 | 7/2012 | Simon et al. |
| 2012/0224970 A1 | 9/2012 | Schumacher et al. |
| 2012/0226097 A1 | 9/2012 | Smith et al. |
| 2012/0234411 A1 | 9/2012 | Scheckel |
| 2012/0245404 A1 | 9/2012 | Smith et al. |
| 2012/0265002 A1 | 10/2012 | Roehn et al. |
| 2013/0041202 A1 | 2/2013 | Toellner |
| 2013/0053622 A1 | 2/2013 | Corbett |
| 2013/0053623 A1 | 2/2013 | Evans et al. |
| 2013/0066140 A1 | 3/2013 | McBride et al. |
| 2013/0085318 A1 | 4/2013 | Toellner |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0129503 A1 | 5/2013 | McBride et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0237744 A1 | 9/2013 | Pfeffer et al. |
| 2013/0245360 A1 | 9/2013 | Schumacher |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0039465 A1 | 2/2014 | Schulz et al. |
| 2014/0067057 A1 | 3/2014 | Callaway et al. |

(56) References Cited

U.S. PATENT DOCUMENTS

| | | |
|---|---|---|
| 2014/0088455 A1 | 3/2014 | Christensen et al. |
| 2014/0148638 A1 | 5/2014 | LaRose et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng et al. |
| 2014/0301822 A1 | 10/2014 | Scheckel |
| 2014/0303596 A1 | 10/2014 | Schumacher et al. |
| 2015/0025558 A1 | 1/2015 | Wulfman et al. |
| 2015/0031936 A1 | 1/2015 | LaRose et al. |
| 2015/0051435 A1 | 2/2015 | Siess et al. |
| 2015/0051436 A1 | 2/2015 | Spanier et al. |
| 2015/0080743 A1 | 3/2015 | Siess |
| 2015/0087890 A1 | 3/2015 | Spanier et al. |
| 2015/0141738 A1 | 5/2015 | Toellner et al. |
| 2015/0141739 A1 | 5/2015 | Hsu et al. |
| 2015/0151032 A1 | 6/2015 | Voskoboynikov |
| 2015/0209498 A1 | 7/2015 | Franono et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0184500 A1 | 6/2016 | Zeng |
| 2016/0250399 A1 | 9/2016 | Tiller et al. |
| 2016/0250400 A1 | 9/2016 | Schumacher et al. |
| 2016/0256620 A1 | 9/2016 | Scheckel et al. |

FOREIGN PATENT DOCUMENTS

| | | |
|---|---|---|
| EP | 1 207 934 | 5/2002 |
| EP | 1 393 762 A1 | 3/2004 |
| EP | 1 591 079 A1 | 11/2005 |
| EP | 2 263 732 | 12/2010 |
| EP | 2 298 374 A1 | 3/2011 |
| FR | 2267800 | 4/1974 |
| GB | 2 239 675 A | 7/1991 |
| JP | S48-23295 | 3/1973 |
| JP | 06-114101 | 4/1994 |
| JP | 10-099447 | 4/1998 |
| TW | 500877 | 9/2002 |
| WO | WO 89/05164 | 6/1989 |
| WO | WO 95/26695 | 10/1995 |
| WO | WO 97/15228 | 5/1997 |
| WO | WO 97/37697 | 10/1997 |
| WO | WO 00/12148 | 3/2000 |
| WO | WO 00/19097 | 4/2000 |
| WO | WO 00/43062 | 7/2000 |
| WO | WO 00/61207 | 10/2000 |
| WO | WO 00/69489 | 11/2000 |
| WO | WO 01/17581 A2 | 3/2001 |
| WO | WO 01/24867 | 4/2001 |
| WO | WO 02/070039 | 9/2002 |
| WO | WO 03/103745 | 12/2003 |
| WO | WO 2005/089674 | 9/2005 |
| WO | WO 2005/123158 | 12/2005 |
| WO | WO 2009/073037 | 6/2009 |
| WO | WO 2009/076460 A2 | 6/2009 |
| WO | WO 2010/127871 | 11/2010 |
| WO | WO 2010/133567 | 11/2010 |
| WO | WO 2010/149393 | 12/2010 |
| WO | WO 2011/035926 | 3/2011 |
| WO | WO 2011/035929 | 3/2011 |
| WO | WO 2011/039091 A1 | 4/2011 |
| WO | WO 2011/076439 | 6/2011 |
| WO | WO 2011/089022 | 7/2011 |
| WO | WO 2012/007140 | 1/2012 |
| WO | WO 2012/007141 | 1/2012 |
| WO | WO 2013/160407 A1 | 10/2013 |
| WO | WO 2014/019274 A1 | 2/2014 |
| WO | WO 2015/063277 | 5/2015 |

OTHER PUBLICATIONS

Abiomed—Recovering Hearts. Saving Lives., Impella 2.5 System, Instructions for Use, Jul. 2007, in 86 sheets.

Aboul-Hosn et al., "The Hemopump: Clinical Results and Future Applications", Assisted Circulation 4, 1995, in 14 pages.

Barras et al., "Nitinol—Its Use in Vascular Surgery and Other Applications," Eur. J. Vasc. Endovasc. Surg., 2000, pp. 564-569; vol. 19.

Biscarini et al., "Enhanced Nitinol Properties for Biomedical Applications," Recent Patents on Biomedical Engineering, 2008, pp. 180-196, vol. 1(3).

Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.

Compendium of Technical and Scientific Information for the HEMOPUMP Temporary Cardiac Assist System, Johnson & Johnson Interventional Systems, 1988, in 15 pages.

Dekker et al., "Efficacy of a New Intraaortic Propeller Pump vs the Intraaortic Balloon Pump, An Animal Study", Chest, Jun. 2003, vol. 123, No. 6, pp. 2089-2095.

Duerig et al., "An Overview of Nitinol Medical Applications," Materials Science Engineering, 1999, pp. 149-160; vol. A273.

European Search Report received in European Patent Application No. 05799883.3, dated May 10, 2011, in 4 pages.

Extended European Search Report received in European Patent Application No. 07753903.9, dated Oct. 8, 2012, in 7 pages.

Extended European Search Report received in European Patent Application No. 13813687.4, dated Feb. 24, 2016, in 6 pages.

Extended European Search Report received in European Patent Application No. 13813867.2, dated Feb. 26, 2016, in 6 pages.

Extended European Search Report received in European Patent Application No. 14779928.2, dated Oct. 7, 2016, in 6 pages.

Federal and Drug Administration 510(k) Summary for Predicate Device IMPELLA 2.5 (K112892), prepared Sep. 5, 2012.

Grech, "Percutaneous Coronary Intervention. I: History and Development," BMJ., May 17, 2003, pp. 1080-1082, vol. 326.

Hsu et al., "Review of Recent Patents on Foldable Ventricular Assist Devices," Recent Patents on Biomedical Engineering, 2012, pp. 208-222, vol. 5.

Ide et al., "Evaluation of the Pulsatility of a New Pulsatile Left Ventricular Assist Device—the Integrated Cardioassist Catheter—in Dogs," J. of Thorac and Cardiovasc Sur, Feb. 1994, pp. 569-0575, vol. 107(2).

Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, pp. 286-290, vol. 16(3).

Impella CP®—Instructions for Use & Clinical Reference Manual (United States only), Abiomed, Inc., Jul. 2014, 148 pages, www.abiomed.com.

Impella LD® with the Impella® Controller—Circulatory Support System—Instructions for Use & Clinical Reference Manual (United States only), Abiomed, Inc., Sep. 2010, 132 pages, www.abiomed.com.

International Preliminary Examination Report received in International Patent Application No. PCT/US2003/04853, dated Jul. 26, 2004, in 5 pages.

International Preliminary Examination Report received in International Patent Application No. PCT/US2003/04401, dated May 18, 2004, in 4 pages.

International Preliminary Report on Patentability and Written Opinion of the International Searching Authority received in International Patent Application No. PCT/US2005/033416, dated Mar. 20, 2007, in 7 pages.

International Preliminary Report on Patentability and Written Opinion of the International Searching Authority received in International Patent Application No. PCT/US2007/007313, dated Sep. 23, 2008, in 6 pages.

International Preliminary Report on Patentability and Written Opinion received in International Patent Application No. PCT/US2014/020878, dated Sep. 15, 2015, in 8 pages.

International Search Report and Written Opinion received in International Patent Application No. PCT/US2005/033416, dated Dec. 11, 2006, in 8 pages.

(56) References Cited

OTHER PUBLICATIONS

International Search Report and Written Opinion received in International Patent Application No. PCT/US2007/007313, dated Mar. 4, 2008, in 6 pages.
International Search Report and Written Opinion received in International Patent Application No. PCT/US2012/020382, dated Jul. 31, 2012, in 11 pages.
International Search Report and Written Opinion received in International Patent Application No. PCT/US2012/020369, dated Jul. 30, 2012, in 10 pages.
International Search Report and Written Opinion received in International Patent Application No. PCT/US2012/020553, dated Aug. 17, 2012, in 8 pages.
International Search Report and Written Opinion received in International Patent Application No. PCT/US2012/020383, dated Aug. 17, 2012; in 9 pages.
International Search Report and Written Opinion received in International Patent Application No. PCT/US2013/040798, dated Aug. 21, 2013, in 16 pages.
International Search Report and Written Opinion received in International Patent Application No. PCT/US2013/040799, dated Aug. 21, 2013, in 19 pages.
International Search Report and Written Opinion received in International Patent Application No. PCT/US2013/040809, dated Sep. 2, 2013, in 25 pages.
International Search Report and Written Opinion received in International Patent Application No. PCT/US2013/048332, dated Oct. 16, 2013, in 17 pages.
International Search Report and Written Opinion received in International Patent Application No. PCT/US2013/048343, dated Oct. 11, 2013, in 15 pages.
International Search Report and Written Opinion received in International Patent Application No. PCT/US2014/020878, dated May 7, 2014, in 13 pages.
International Search Reort and Written Opinion received in International Patent Application No. PCT/US2015/026013, dated Jul. 8, 2015, in 12 pages.
International Search Report and Written Opinion received in International Patent Application No. PCT/US2015/026014, dated Jul. 15, 2015, in 13 pages.
International Search Report and Written Opinion received in International Patent Application No. PCT/US2015/026025, dated Jul. 20, 2015, in 12 pages.
International Search Report and Written Opinion received in International Patent Application No. PCT/US2015/025959, dated Aug. 28, 2015, in 16 pages.
International Search Report and Written Opinion received in International Patent Application No. PCT/US2015/025960, dated Sep. 3, 2015, in 15 pages.
International Search Report and Written Opinion received in International Patent Application No. PCT/US2015/045370, dated Nov. 18, 2015, in 12 pages.
International Search Report and Written Opinion received in International Patent Application No. PCT/US2016/014371, dated May 2, 2016, in 18 pages.
International Search Report and Written Opinion received in International Patent Application No. PCT/US2016/014379, dated Jul. 25, 2016, in 19 pages.
International Search Report and Written Opinion received in International Patent Application No. PCT/US2016/014391, dated May 2, 2016, in 17 pages.
International Search Report received in International Patent Application No. PCT/US2003/004401, dated Nov. 10, 2003, in 9 pages.
International Search Report received in International Patent Application No. PCT/US2003/004853, dated Jul. 3, 2003, in 3 pages.
International Search Report Written Opinion received in International Patent Application No. PCT/US2010/040847, dated Dec. 14, 2010, in 17 pages.
JOMED Reitan Catheter Pump RCP, Percutaneous Circulatory Support, in 10 pages, believed to be published prior to Oct. 15, 2003.
JOMED Reitan Catheter Pump RCP, Feb. 18, 2003, in 4 pages.
Krishnamani et al., "Emerging Ventricular Assist Devices for Long-Term Cardiac Support," National Review, Cardiology, Feb. 2010, pp. 71-76, vol. 7.
Kunst et al., "Integrated unit for programmable control of the 21F Hemopump and registration of physiological signals," Medical & Biological Engineering & Computing, Nov. 1994, pp. 694-696.
Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).
Minimally Invasive Cardiac Assist JOMED Catheter PumpTM, in 6 pages, believed to be published prior to Jun. 16, 1999.
Morgan, "Medical Shape Memory Alloy Applications—The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD," The International Journal of Artificial Organs, 1997, pp. 277-284; vol. 20(5).
Nishimura et al, "The Enabler Cannula Pump: A Novel Circulatory Support System," The International Journal of Artificial Organs, 1999, pp. 317-323; vol. 22(5).
Nullity Action against the owner of the German part DE 50 2007 005 015.6 of European patent EP 2 047 872 B1, dated Jul. 13, 2015, in 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Rakhorst et al., "In Vitro Evaluation of the Influence of Pulsatile Intraventricular Pumping on Ventricular Pressure Patterns," Artificial Organs, 1994, pp. 494-499, vol. 18(7).
Reitan, Evaluation of a New Percutaneous Cardiac Assist Device, Department of Cardiology, Faculty of Medicine, Lund University, Sweden, 2002, in 172 pages.
Reitan et al., "Hemodynamic Effects of a New Percutaneous Circulatory Support Device in a Left Ventricular Failure Model," ASAIO Journal, 2003, pp. 731-736, vol. 49.
Reitan et al., "Hydrodynamic Properties of a New Percutaneous Intra-Aortic Axial Flow Pump," ASAIO Journal 2000, pp. 323-328.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
Sieß et al., "Hydraulic refinement of an intraarterial microaxial blood pump", The International Journal of Artificial Organs, 1995, vol. 18, No. 5, pp. 273-285.
Sieß, "Systemanalyse und Entwicklung intravasaler Rotationspumpen zur Herzunterstützung", Helmholtz-Institut fur Blomedixinische Technik an der RWTH Aachen, Jun. 24, 1998, in 105 pages.
Siess et al., "Basic design criteria for rotary blood pumps," H. Masuda, Rotary Blood Pumps, Springer, Japan, 2000, pp. 69-83.

(56) References Cited

OTHER PUBLICATIONS

Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.

Siess et al., "From a lab type to a product: A retrospective view on Impella's assist technology," Artificial Organs, 2001, pp. 414-421, vol. 25, No. 5, Blackwell Science, Inc., International Society for Artificial Organs.

Siess et al., "System analysis and development of intravascular rotation pumps for cardiac assist," Dissertation, Shaker Verlag, Aachen, 1999, 39 pages.

Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).

Sokolowski et al., "Medical Applications of Shape Memory Polymers," Biomed. Mater. 2007, pp. S23-S27, vol. 2.

"Statistical Analysis and Clinical Experience with the Recover® Pump Systems", Impella CardioSystems GmbH, Sep. 2005, 2 sheets.

Stoeckel et al., "Self-Expanding Nitinol Stents—Material and Design Considerations," European Radiology, 2003, in 13 sheets.

Stolinski et al., "The heart-pump interaction: effects of a microaxial blood pump," International Journal of Artificial Organs, 2002, pp. 1082-1088, vol. 25, Issue 11.

Supplemental European Search Report received from the European Patent Office in EP Application No. EP 05799883 dated Mar. 19, 2010, 3 pages.

Takagaki et al., "A Novel Miniature Ventricular Assist Device for Hemodynamic Support," ASAIO Journal, 2001, pp. 412-416; vol. 47.

Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).

Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.

Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).

Verkerke et al., "Numerical Simulation of the Pulsating Catheter Pump: A Left Ventricular Assist Device," Artificial Organs, 1999, pp. 924-931, vol. 23(10).

Verkerke et al., "The PUCA Pump: A Left Ventricular Assist Device," Artificial Organs, 1993, pp. 365-368, vol. 17(5).

Wampler et al., "The Sternotomy Hemopump, A Second Generation Intraarterial Ventricular Assist Device," ASAIO Journal, 1993, pp. M218-M223, vol. 39.

Weber et al., "Principles of Impella Cardiac Support," Supplemental to Cardiac Interventions Today, Aug./Sep. 2009.

Written Opinion received in International Patent Application No. PCT/US2003/04853, dated Feb. 25, 2004, 5 pages.

\* cited by examiner

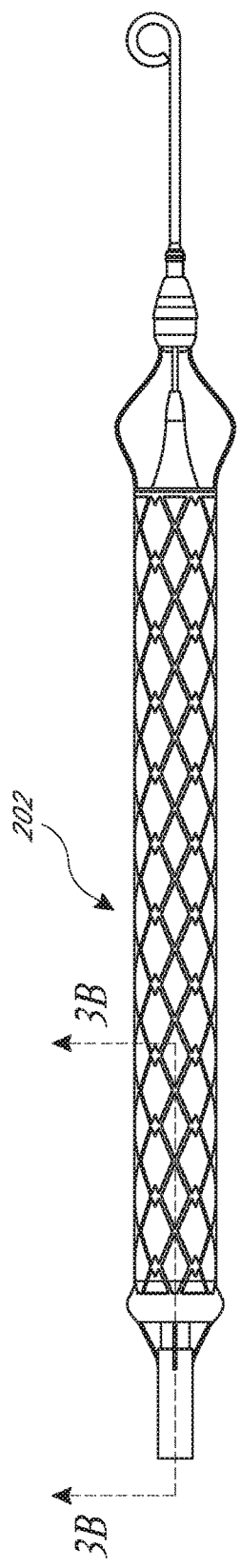
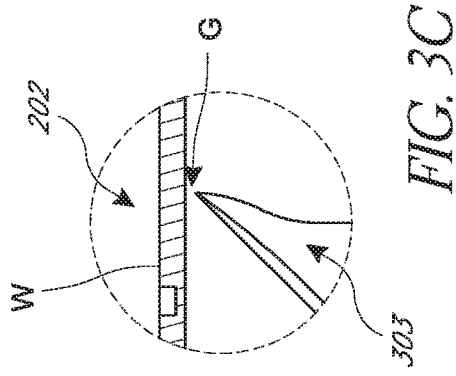
FIG. 3A
FIG. 3B
FIG. 3C

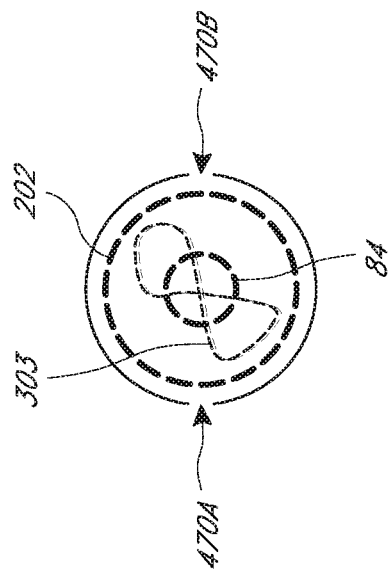
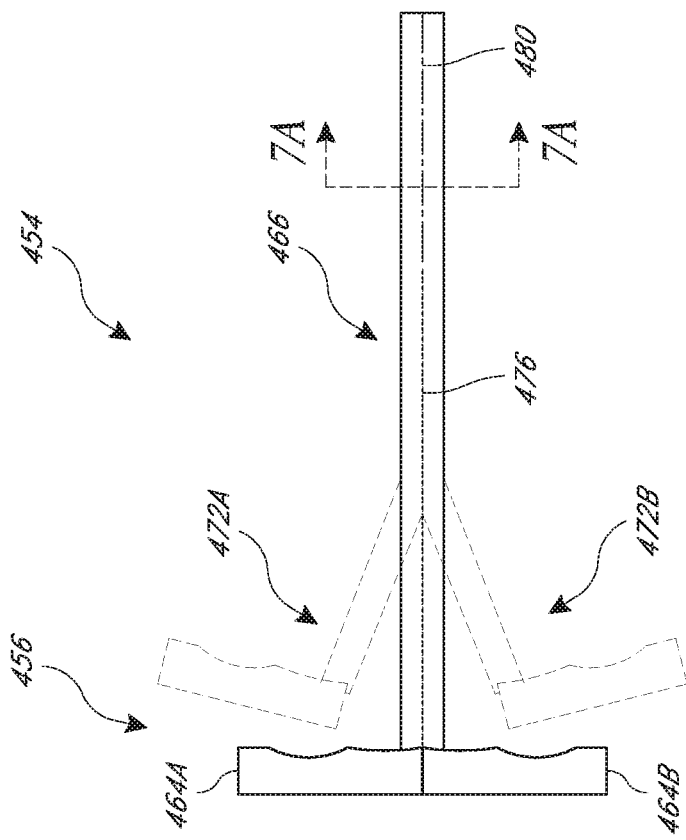

CATHETER PUMP INTRODUCER SYSTEMS AND METHODS

CROSS-REFERENCE TO RELATED APPLICATIONS

This application claims priority to U.S. Provisional Patent Application No. 61/979,937, filed Apr. 15, 2014, the contents of which are incorporated by reference herein in their entirety and for all purposes.

BACKGROUND OF THE INVENTION

Field of the Invention

This application is directed to pumps for mechanical circulatory support of a heart. In particular, this application is directed to devices used to position such pumps in a patient using percutaneous or catheter techniques.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e. higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15FR or 12FR incision. In one aspect, there is a need for a heart pump that can be placed minimally-invasively and provide high flow rates but minimize obstruction of the vasculature through which the pump is placed. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow while minimizing the likelihood of hemolysis at high rotational speeds. These and other problems are overcome by the inventions described herein.

Further, there is a need for providing an operative device of the pump capable of pumping blood at high flow rates while reducing the risk of hemolysis at the operative device. For example, when an impeller assembly is provided at the operative device, the high rate of rotation of the impeller may cause hemolysis, as blood flows past the high-speed impeller. Accordingly, there is a need for reducing the risk of hemolysis at the operative device of the pump, particularly when movable components are disposed at the operative device.

SUMMARY

There is an urgent need for a pumping device that can be inserted percutaneously and also provide full cardiac rate flows of the left, right, or both the left and right sides of the heart when called for.

In one embodiment, a catheter system for a catheter pump is provided that includes an elongate body an impeller assembly, and a sheath. The elongated catheter body has a distal portion that includes an expandable cannula. The expandable cannula has an inlet and an outlet. The expandable cannula has a delivery profile and an operational profile larger than the delivery profile. The impeller assembly includes an impeller shaft and an impeller body that includes one or more blades. The impeller blade(s) draw fluid blood into the cannula when rotated in the fluid. The sheath has a cannula retention zone disposed over the expandable cannula and a separation zone. The cannula retention zone has a first configuration in which it is adapted to retain the expandable cannula in the delivery profile. The wherein the system is adapted to separate the separation zone into a first portion and a second portion disposed across a gap, the gap enabling the elongate catheter body to pass between the first and second portion so that the sheath can be removed from the elongate catheter body.

In another embodiment, a method is disclosed. The method can comprise advancing into the vasculature a catheter assembly. The catheter assembly can include an expandable cannula having an expandable impeller disposed therein and a sheath having a cannula retention portion disposed over the expandable cannula and the expandable impeller. The cannula retention portion can retain the expandable cannula and the expandable impeller in a low profile configuration. The method can further include providing relative motion between the sheath and the expandable cannula to expose the expandable cannula to permit the expandable cannula to expand to a high profile configuration. The high profile configuration can have a larger width than the low profile configuration. The first and second portions of the sheath can be separated along a longitudinal portion thereof to create a gap therealong. The method can include passing the elongate body through the gap to cause the sheath to be removed from the catheter assembly.

In yet another embodiment, a method is disclosed. The method can comprise disposing an introducer sheath in the vasculature of a patient. The method can include introducing a catheter assembly into the proximal end of the introducer sheath and into the vasculature through the introducer sheath. The catheter assembly can include an elongate body having an expandable cannula coupled with a distal end thereof. The catheter assembly can have an expandable impeller being journaled for rotation in the expandable cannula. The expandable impeller can be expanded for operation in a source of blood. The elongate body can be retracted into the introducer sheath such that the expandable cannula engages a distal end of the introducer sheath. Relative motion can be provided between the introducer sheath and the expandable cannula to compress the expandable cannula. The introducer sheath and the catheter assembly can be removed from the patient.

BRIEF DESCRIPTION OF THE DRAWINGS

A more complete appreciation of the subject matter of this application and the various advantages thereof can be realized by reference to the following detailed description, in which reference is made to the accompanying drawings in which:

FIGS. 3A-3C illustrate the relative position of an impeller blade and an inner surface of an impeller housing or cannula in an undeflected configuration;

FIGS. 7 & 7A illustrate more details of a removeable sheath and the relationship of the sheath to components that it houses during introduction.

Figure 1:
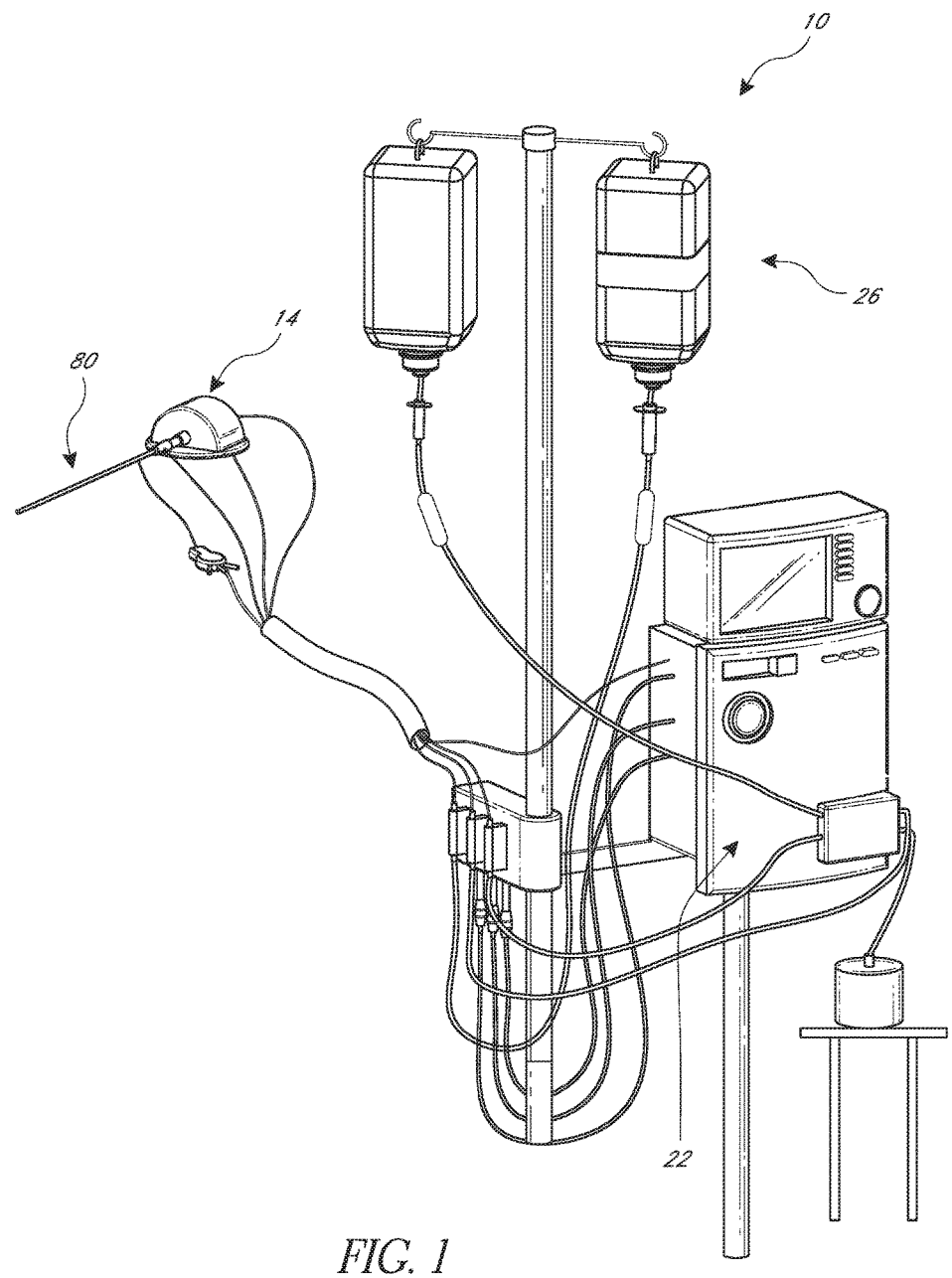
FIG. 1 illustrates one embodiment of an extracorporeal portion of a catheter pump configured for percutaneous application and operation.

More detailed descriptions of various embodiments of components for heart pumps useful to treat patients experiencing cardiac stress, including acute heart failure, are set forth below.

DETAILED DESCRIPTION OF THE PREFERRED EMBODIMENT

This application is directed to apparatuses for inducing motion of a fluid relative to the apparatus. In particular, the disclosed embodiments generally relate to various configurations of devices for percutaneously delivering a distal portion of a catheter pump. As discussed in greater detail below, such devices provide reduced or minimized blood flow obstruction in the vasculature in which the catheter pump is disposed. For example, in the disclosed embodiments, one or more layers of a distal portion of the catheter assembly can be removed to reduce the profile of the distal portion during operation of the pump. In some embodiments a temporary protector is provided for expandable and/or delicate structures of a catheter pump assembly. In some of the disclosed embodiments, the function of collapsing an expandable portion of the catheter pump and of providing initial access to the vasculature is performed by the same structure.

I. Catheter Pump System and Method

FIGS. 1-4 show aspects of one embodiment of a catheter pump 10 that can provide high performance flow rates. Various additional aspects of the pump and associated components are similar to those disclosed in U.S. Pat. Nos. 7,393,181, 8,376,707, 7,841,976, 8,535,211, 8,597,170, 8,485,961, 8,591,393, 7,022,100, and 7,998,054 and U.S. Pub. Nos. 2012/0178986, 2013/0303970, 2013/0303969, 2013/0303830, 2014/0012065, and 2014/0010686 the entire contents of which are incorporated herein for all purposes by reference. In addition, this application incorporates by reference in its entirety and for all purposes the subject matter disclosed in each of the following concurrently filed applications: U.S. patent application Ser. Nos. 14/203,978, which corresponds to attorney docket no. THOR.084A, entitled "FLUID HANDLING SYSTEM," and 14/209,889, which corresponds to attorney docket no. THOR.097A, entitled "CATHETER PUMP ASSEMBLY INCLUDING A STATOR," filed on Mar. 13, 2014 and PCT Patent Application Nos. PCT/US2014/020790 which corresponds to attorney docket no. THOR.084WO, entitled "FLUID HANDLING SYSTEM," and PCT/US2014/020878 which corresponds to attorney docket no. THOR.097WO, entitled "CATHETER PUMP ASSEMBLY INCLUDING A STATOR," filed on Mar. 5, 2014.

A. Catheter Pump System

The pump 10 includes a motor driven by a controller 22. The controller 22 directs the operation of the motor 14 and an infusion system 26 that supplies a flow of infusate in the pump 10. A catheter system 80 that can be coupled with the motor 14 houses an impeller within a distal portion thereof. The catheter system 80 has a coupling 90 that can be engaged with the motor 14 in certain embodiments. In various embodiments, the impeller is rotated by the motor 14 when the pump 10 is operating. For example, the motor 14 can be disposed outside the patient. In some embodiments, the motor 14 is separate from the controller 22, e.g., to be placed closer to the patient. In other embodiments, the motor 14 is part of the controller 22. In still other embodiments, the motor is miniaturized to be insertable into the patient. Such embodiments allow the drive shaft to be much shorter, e.g., shorter than the distance from the aortic valve to the aortic arch (about 5 cm or less). Some examples of miniaturized motors catheter pumps and related components and methods are discussed in U.S. Pat. Nos. 5,964,694; 6,007,478; 6,178, 922; and 6,176,848, all of which are hereby incorporated by reference herein in their entirety for all purposes.

Figure 2:
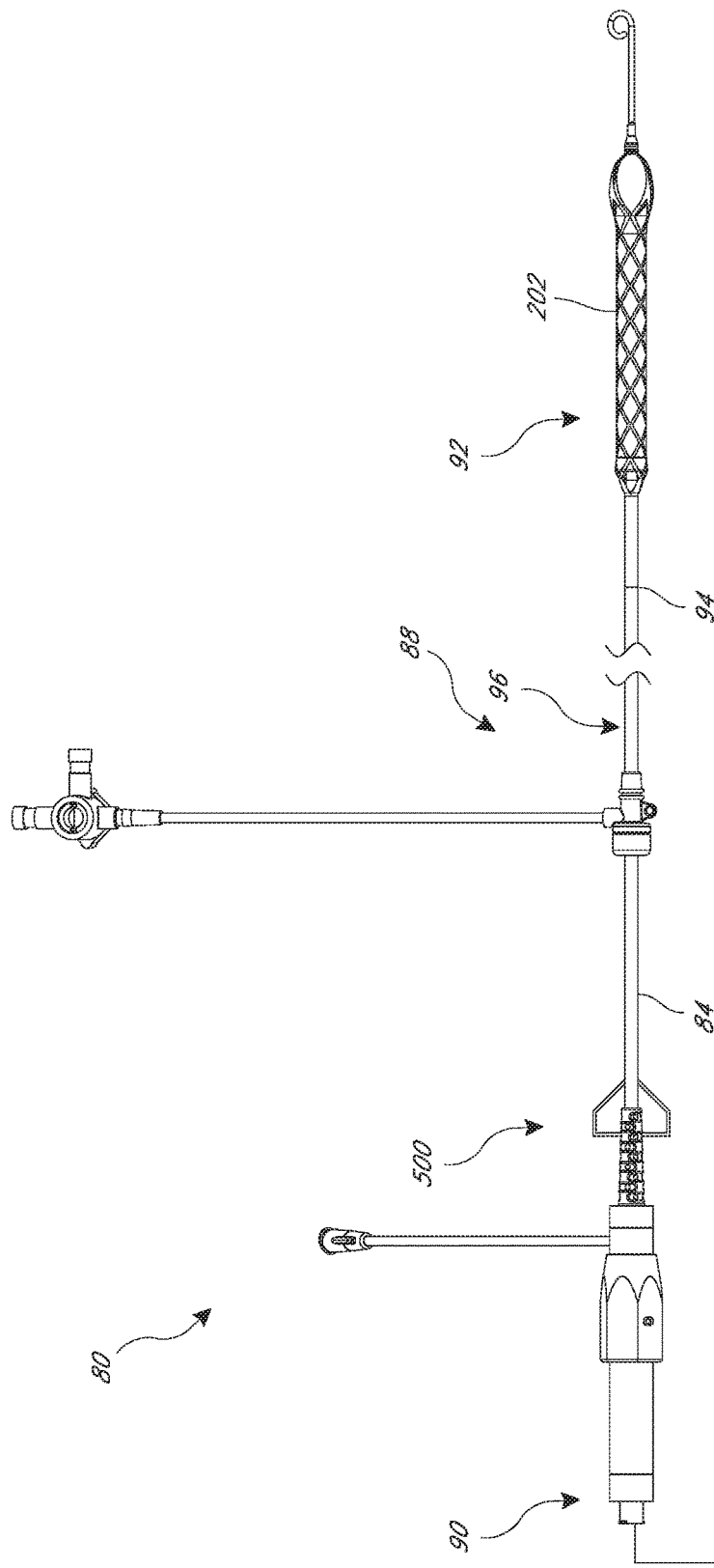
FIG. 2 is a plan view of one embodiment of a catheter assembly adapted to be used with the catheter pump of FIG. 1, a distal portion of which is inserted into the vasculature of a patient in use.
Figure 4:
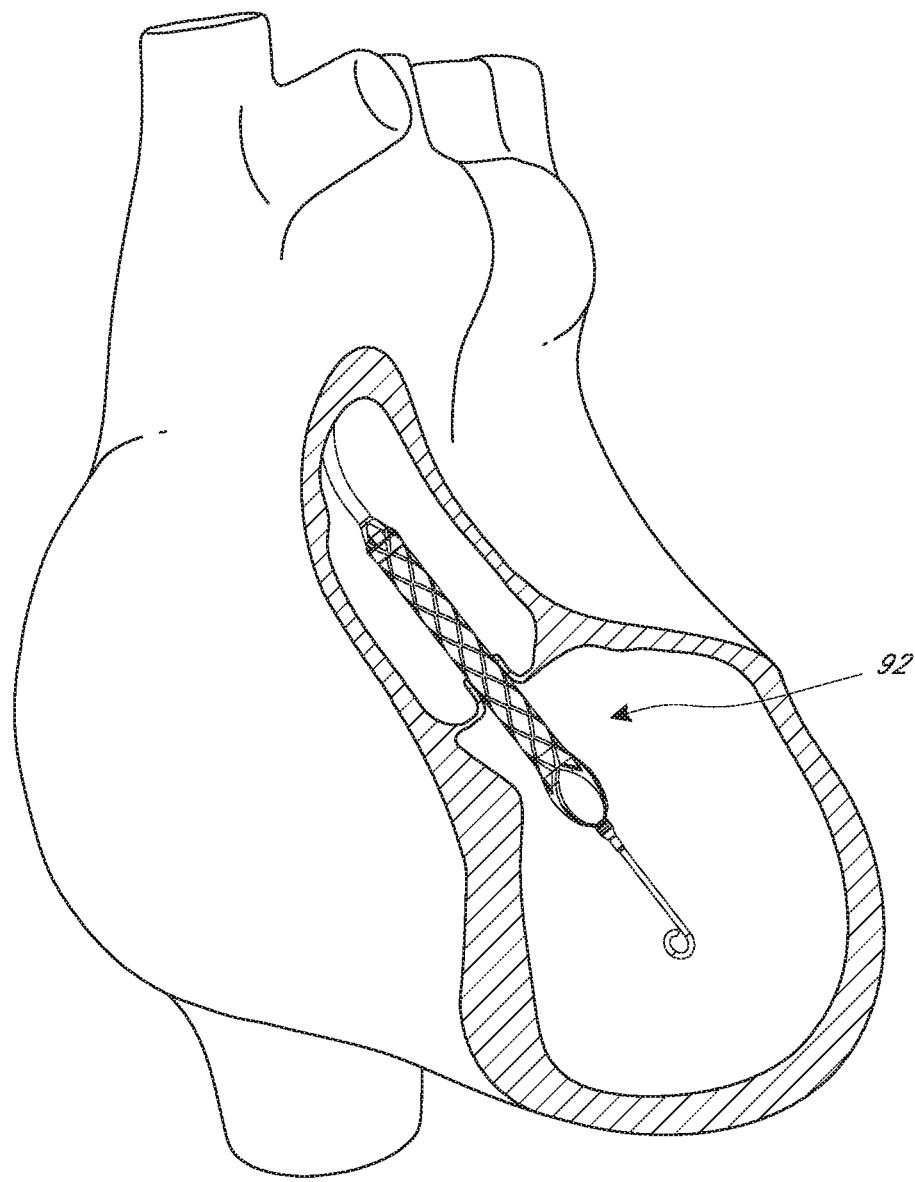
FIG. 4 shows the catheter assembly similar to that of FIG. 2 in position within the anatomy.

FIG. 2 shows features that facilitate small blood vessel percutaneous delivery of a high performance pump head, including a pump head capable of producing up to and in some cases exceeding normal cardiac output in all phases of the cardiac cycle. In particular, the catheter system 80 includes a catheter body 84 and a sheath assembly 88. In one embodiment a blood flow assembly 92 (sometimes referred to herein as an impeller assembly) is coupled with the distal end of the catheter body 84. At least a portion of the blood flow assembly 92 is expandable and collapsible. For example, the blood flow assembly 92 can include an expandable and collapsible cannula 202. The cannula 202 can be formed of a superelastic material, and in some embodiments, may have various shape memory material properties. The blood flow assembly 92 also can include an expandable and collapsible impeller 300 (see FIGS. 3B-3C). The cannula 202 and impeller 300 are discussed more below. In the collapsed state, the distal end of the catheter system 80 can be advanced to the heart, for example, through an artery. In the expanded state the blood flow assembly 92 is able to pump or output blood at high flow rates. FIGS. 2-4 illustrate the expanded state of one embodiment. The collapsed state can be provided by advancing a distal end 94 of an elongate body 96 of the sheath assembly 88 distally over the cannula of the blood flow assembly 92 to cause the blood flow assembly 92 to collapse. In embodiments below, variations of the sheath assembly 88 can be removed at least in part. In one variation discussed further below, a separation device 500 is provided on the catheter system 80 to induce or ease segmentation of the sheath assembly 88 or portions thereof into separate parts. The separation device 500 can include one or more fins that are disposed on the proximal portion of the elongate body 84 of the catheter system 80. The fins can be rigid protrusions of disposed on at least partially on the body 84 or disposed on a portion of the coupling 90. The separation device 500 can be disposed at least in part on a strain relief portion disposed between the coupling 90 and the elongate body 84. As discussed further below, in such embodiments other structures are used to collapse the cannula 202 and the impeller 300 after these components are expanded inside the patient. This provides an outer profile throughout the catheter assembly 80 that is of small diameter, for example a catheter size of about 12.5 Fr. This also provides that the operational profile of the catheter assembly can be reduced or minimized as discussed further below.

B. Impeller and Cannula Features, Deployment, and Operation

With reference to FIGS. 3A-3C, the operative device of the pump can include the impeller 300, which has one or more blades 303. The one or more blades 303 can extend from an impeller hub 301. It can be desirable to increase the flow rate of the heart pump while ensuring that the impeller 300 can be effectively deployed within a subject. For example, an impeller can include one or more blades 303 that are configured to be inserted into a subject in a stored, or compressed, configuration. When the impeller 300 is positioned in the desired location, e.g., a chamber of a subject's heart as shown in FIG. 4, the blade(s) 303 of the impeller 300 can self-expand into a deployed or expanded configuration, in which the blade(s) 303 extends radially from a hub 301.

As shown in FIGS. 3A-3B, the impeller 300 can be positioned within the cannula or housing 202. A free end of the blades 303 can be separated from the wall W of the housing 202 by a tip gap G. The housing 202 can also have a stored, or compressed configuration, and a deployed or expanded configuration. The housing 202 and impeller 300 may deploy from the stored configurations from within the sheath assembly 88 into the expanded configuration. In such implementations, the sheath assembly 88 can keep the blade(s) 303 and the housing 202 compressed until the blade(s) 303 and housing 202 are urged from within a lumen of the sheath assembly 88. Once the blade(s) 303 are released from the sheath assembly, the blade(s) 303 can self-expand to a deployed configuration using strain energy stored in the blades 303 due to deformation of the blade(s) 303 within the sheath assembly 88. The expandable housing 202 may also self-deploy using stored strain energy after being urged from the sheath. The combined energy stored in the expandable housing 202 and blades 303 generates a force that preferably is opposed by the distal portion of the elongate body 96 of the sheath assembly 88. Thus, this portion should be of robust design to avoid premature deployment of the housing 202 and blades 303, e.g., prior to positioning in the heart or other source of blood.

Variations of the sheath assembly 88 are configured to be removed (e.g., by one or more seams) from the patient's body and in some cases entirely from the catheter body 84 to lower the profile of the portion of the catheter system 80 in the body. Removing the sheath assembly 88 has a number of benefits discussed further below including opening up space in the vasculature for blood flow around the remainder of the catheter system 80 that remains in the vasculature after the sheath assembly is removed. By providing such additional flow, the ability of the patient to tolerate the presence of the implanted portions of the pump 10 is enhanced. Catheter pumps typically have a large diameter relative to the access vessels and thus pose a meaningful risk of limb ischemia and other complications. Accordingly, even small reductions in diameter and increased blood flow around the device can be advantageous. Also, by enabling a portion of the catheter pump that is initially placed in the access vessel to be removed, a less invasive access technique can be provided. For example, the skin and blood vessel puncture can be smaller in size be removing one or more layers during or shortly after placement of the pump. For example, the presence of the body of the sheath contributes to the overall profile of the assembly passing through the skin and into the blood vessel. The skin and blood vessel can stretch for a short time which can enable the puncture to be the same size or even a bit smaller than the initial profile of the catheter assembly. By removing the sheath 88, the degree of stretch, the time during which the punctured tissues are stretched or both the degree and time are reduced which enables the punctures to be smaller and/or to avoid surgical cut-down while maintaining the size of the internal components (e.g., cannula, impeller, and drive shaft). These and other benefits and structures are discussed further below.

In the stored configuration, the impeller 300 and housing 202 have a diameter that is preferably small enough to be inserted percutaneously into a patient's vascular system. Thus, it can be advantageous to fold the impeller 300 and housing 202 into a small enough stored configuration such that the housing 202 and impeller 300 can fit within the patient's veins or arteries, particularly small veins or arteries that are peripheral and superficial, e.g., femoral veins or arteries, jugular and subclavian veins, radial and subclavian arteries. In some embodiments, therefore, the impeller 300 can have a diameter in the stored configuration corresponding to a catheter size between about 8 Fr and about 21 Fr. In one implementation, the impeller 300 can have a diameter in the stored state corresponding to a catheter size of about 7 Fr. In one implementation, the impeller 300 can have a diameter in the stored state corresponding to a catheter size of about 9 Fr. In one implementation, the impeller 300 can have a diameter in the stored state corresponding to a catheter size of about 10 Fr. In other embodiments, the impeller 300 can have a diameter in the stored configuration between about 12 Fr and about 21 Fr. For example, in one embodiment, the impeller 300 can have a diameter in the stored configuration corresponding to a catheter size of about 12-12.5 Fr.

When the impeller 300 is positioned within a chamber of the heart, however, it can be advantageous to expand the impeller 300 to have a diameter as large as possible in the expanded or deployed configuration. In general, increased diameter of the impeller 300 advantageously increases flow rate through the pump at a given rotational speed. A larger diameter impeller can also lead to an improved ratio of flow rate to hemolysis rate. In some implementations, the impeller 300 can have a diameter corresponding to a catheter size greater than about 12 Fr in the deployed configuration. In other embodiments, the impeller 300 can have a diameter corresponding to a catheter size greater than about 21 Fr in the deployed or expanded configuration.

In various embodiments, it can be important to increase the flow rate of the heart pump while ensuring that the operation of the pump does not harm the subject. For example, increased flow rate of the heart pump can advantageously yield better outcomes for a patient by improving the circulation of blood within the patient. Furthermore, the pump should avoid damaging the subject. For example, if the pump induces excessive shear stresses on the blood and fluid flowing through the pump (e.g., flowing through the cannula), then the impeller can cause damage to blood cells, e.g., hemolysis. A high hemolysis rate over an extended period can lead to negative outcomes and complications for the subject like stroke, excessive bleeding, anemia, and hypertension. Also, the presence of the distal portion of the catheter system 80 within the body is at least partially obstructive. That is, the catheter body 84 blocks flow to an extent, e.g., to peripheral regions of the body and smaller branch arteries when applied in the arterial vasculature. The distal end 94 of the sheath assembly 88 also presents a blocking surface to blood following the outer surface of the body 84. As will be explained below, various cannula, system, and/or impeller parameters can affect the pump's flow rate as well as conditions within the subject's body.

When activated, the pump 10 can effectively increase the flow of blood out of the heart and through the patient's vascular system. In various embodiments disclosed herein, the pump 10 can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

C. Exemplary Left Ventricle Support Application

FIG. 4 illustrates one use of the catheter pump 10. A distal portion of the pump 10, which can include an impeller assembly 92, is placed in the left ventricle (LV) of the heart to pump blood from the LV into the aorta. The pump 10 can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the pump 10 in the heart is by percutaneous access and delivery using the Seldinger technique or other methods familiar to cardiologists. These approaches enable the pump 10 to be used in emergency medicine, a catheter lab and in other non-surgical settings. Inventive variations of these methods are discussed in connection with FIGS. 13-18 below. Modifications can also enable the pump 10 to support the right side of the heart. Example modifications that could be used for right side support include providing delivery features and/or shaping a distal portion that is to be placed through at least one heart valve from the venous side, such as is discussed in U.S. Patent and Patent Publication Nos. 6,544,216; U.S. Pat No. 7,070,555; and US 2012-0203056A1, all of which are hereby incorporated by reference herein in their entirety for all purposes.

II. Reducing the Catheter Assembly Profile in Operation

As noted above, one aspect of biocompatibility of the pump 10 is the degree to which it obstructs blood flow in the patient. That is, the catheter assembly 80 takes up some of the cross-sectional area of the blood vessels in which it is disposed. If the space occupied by one or more layers can be reduced or eliminated in one or more phases of operation of the pump 10 the flow of blood through the vasculature in which the pump is disposed and to branch vessels will be improved. Furthermore, while the sheath assembly 88 is very useful in maintaining the impeller assembly 92 in a low profile configuration for delivery, it is unnecessary during the actual operation of the pump 10. Because the distal end 94 of the sheath assembly 88 has some thickness it will necessarily create blockage and a disturbance in the flow of blood along the catheter body 84. That is blood may be flow in an organized manner along the body 84 just upstream of the distal end 94 but will be disrupted at the distal face of the distal end 94.

A. Removable Retainer For Impeller Assembly

Figure 5:
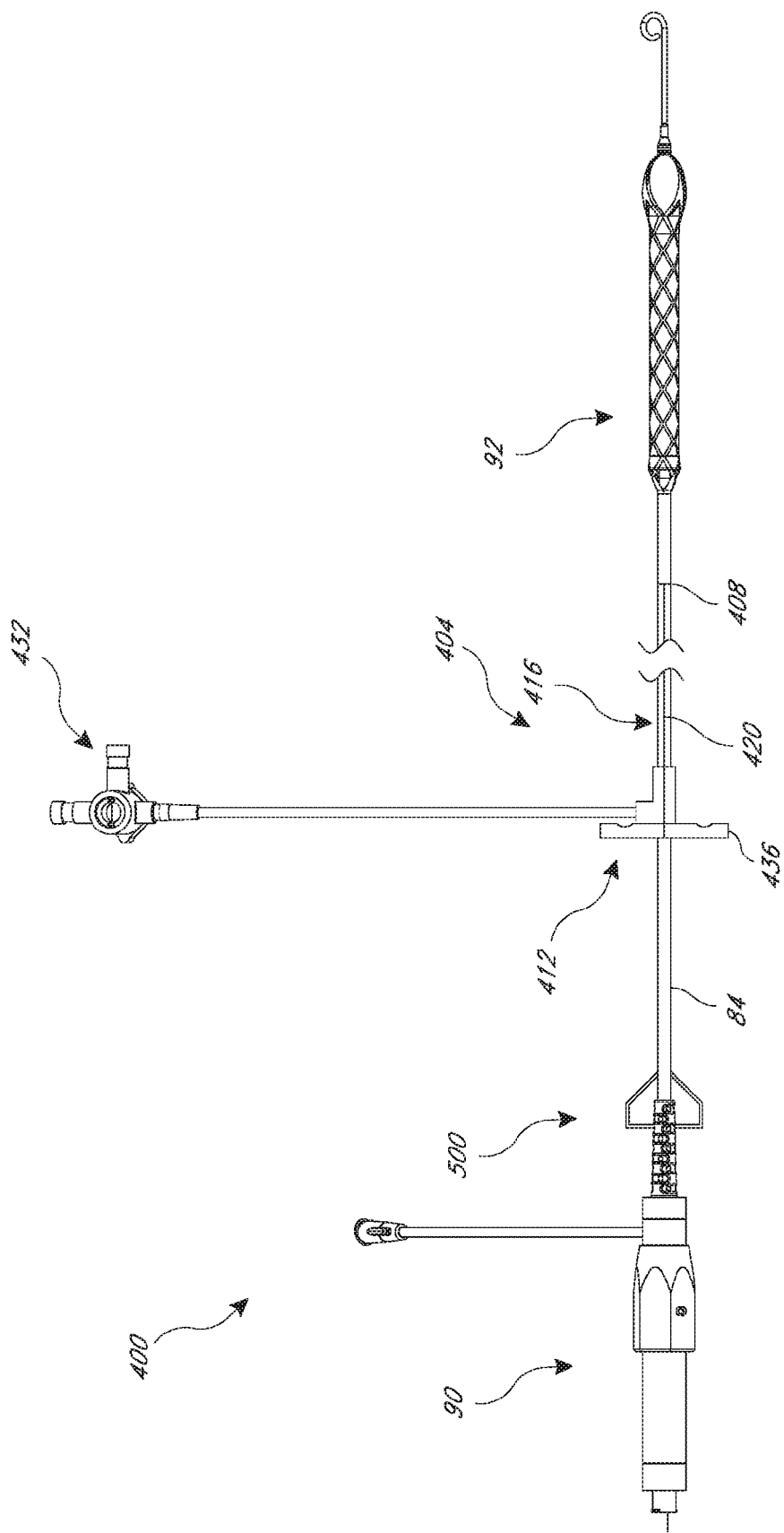
FIG. 5 shows an embodiment of a catheter assembly similar to that of FIG. 2 with a sheath that can be removed from the vasculature of a patient while the working end of the pump is in operation.

FIG. 5 shows a catheter assembly 400 similar to the catheter assembly 80 except that the catheter assembly 400 is made lower profile by configuring at least one layer to be removed before or during operation of the pump. The assembly 400 includes a sheath assembly 404 that can be disposed over the catheter body 84. The sheath assembly 404 includes a distal end 408, a proximal end 412, and an elongate body 416 that extends between the distal and proximal ends 408, 412. The elongate body 416 has at least one lumen disposed therein. A lumen in the elongate body 416 can house the elongate body 84 of the catheter assembly 400. The elongate body 84 can be disposed in the lumen of the elongate body 416 permitting relative movement of the elongate bodies 84, 416 as discussed below. In one embodiment, a lumen is provided in the elongate body 416 for sensing pressure at the distal end 408. In one embodiment, a pressure sensing lumen is contiguous with the lumen within which the elongate body 84 is disposed. In one embodiment, a pressure sensing lumen is separate from the lumen within which the elongate body 84 is disposed.

At least a portion of the sheath assembly 404 is configured to separate from the elongate body 84 in a controlled manner at a selected time. This enables the catheter assembly 400 to be delivered as discussed below and then to permit the sheath assembly 404 to be removed from the body. In one embodiment, a separation zone 420 is provided along the elongate body 416 to enable the elongate body 416 to be opened such that the elongate body 84 can pass through the separation zone 420. In one embodiment, the separation zone 420 enables the elongate body 416 to be separated into a plurality of pieces or segments. In one embodiment, the separation zone 420 comprises a linear seam disposed along the elongate body 416. The separation zone 420 comprises two seams in one embodiment, one of the seams disposed along a first later side of the elongate body 416 and another of the seams disposed along a second later side of the elongate body 416. Two of a plurality of seams can be disposed at 180 degrees apart from each other on the elongate body 416. FIGS. 7 and 7A illustrate opposed seams in more detail, as discussed further below. In one embodiment the separation zone 420 extends from the distal end 408 proximally toward, and in some cases entirely to, the proximal end 412. In another embodiment, the separation zone 420 extends from the proximal end 412 toward the distal end 404 of the elongate body 416.

The separation zone or zones 420 can have any suitable configuration that facilities separating the elongate body 416 into a plurality of pieces or that facilitates changing the configuration of the elongate body 416 from a tubular body to one or more sheet-like body. An advantage of such separation is that the sheath assembly 404 can be removed from the catheter assembly 400 without removing the motor coupling 90 from the proximal end of the system 400 and without greatly lengthening the elongate body 84.

In another embodiment, the separation zone 420 extends along the elongate body 416 and has a distal end that is proximal of the distal end 404. By spacing the distal end of the separation zone 420 from the distal end 408 of the elongate body 416 the outward load or shear or separation force that can be borne by the elongate body 416 can be greater adjacent to the distal end thereof. In one embodiment, the elongate body 416 can be configured such that a first outward force, or shear or separation force can be borne in a region adjacent to the proximal end 412 and a second outward force, shear, or separation force greater than the first outward force, shear, or separation force can be borne by the elongate body 416 adjacent to the distal end 408.

Different outward, shear, or separation force capability can be provided in any suitable manner. For example, the separation zone 420 can have a first seam in a proximal portion of the elongate body 416 and a second seam in a distal portion of the elongate body 416. The first and second seams can be disposed along a continuous line or plane, e.g., along an axis parallel to the longitudinal axis of the elongate body 416. The first seam can have a first plurality of bridges separated by space and the second seams can have a second plurality of bridges separated by space, the dimension of the bridges along the longitudinal axis being greater in the second seam than in the first seam. The first seam can have a first plurality of bridges spanning between and coupling expanses of the elongate body 416 on opposite sides of the separation zone, the bridges being separated by space. The second seams can have a second plurality of such bridges separated by space. The dimension of the bridges along the longitudinal axis of the separation zone 420 can be greater in the second seam than in the first seam. In another embodiment, the radial thickness (e.g., wall thickness or dimension transverse to the longitudinal axis) is greater in the second seam than in the first seam.

Figure 5A:
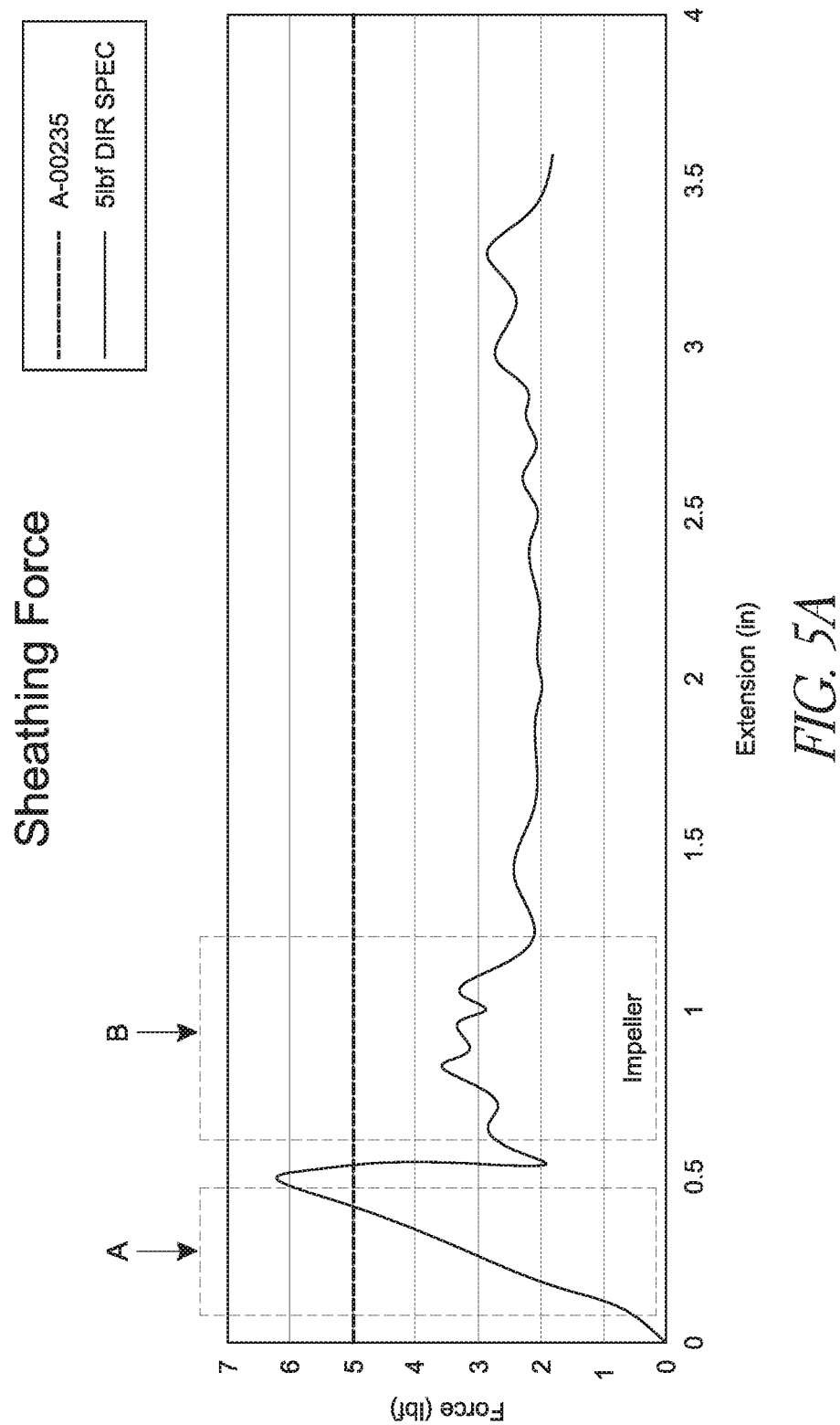
FIG. 5A shows a graph of an axial force that may be required to be applied to an outer sheath.

In one embodiment, a first lateral separation zone is provided along a first lateral side of the elongate body 416 and a second lateral separation zone is provided along a second lateral side of the elongate body 416. The first and second lateral sides can oppose each other, e.g., by being about 180 degrees apart. This is illustrated in connection with the embodiment of FIGS. 7 and 7A. The first and second lateral separation zones can each have a composite seam. The composite seam can include a first portion adjacent the proximal end and a second portion adjacent to the distal end. The second portion can have a higher resistance to separation along the second portion than is provided in the first portion. By providing higher resistance to separation toward the distal end of the sheath assembly 404, e.g., with a composite seam, the sheath assembly can be configured to bear the outwardly directed load from the impeller assembly 92 without inadvertently or prematurely tearing or separating. In some embodiments, the sheath assembly can be configured such that a tear away or separation force is small enough to facilitate separation or tearing by a user, while remaining high enough such that the cannula expansion force does not prematurely induce tearing or separation. For example, the assembly can be configured such that the tearing or separation force can be greater than the forces illustrated in FIG. 5A. FIG. 5A shows a graph of an axial force that may be required to be applied to an outer sheath, such as by the sheath assembly 88, disposed about the catheter body as the sheath assembly 88 is advanced distally along the cannula. Additional details associated with FIG. 5A may be found in FIG. 17 and described in the associated disclosure of U.S. Patent Publication No. US 2014/0012065, which is incorporated by reference herein in its entirety and for all purposes.

FIG. 5 shows that the sheath assembly 404 can include a side branch 432 extending from a hub 436. The side branch 432 can serve one or more of several purposes. For example, the side branch 432 can have a lumen in fluid communication with a lumen disposed within the elongate body 416. A fluid connector can be disposed at the proximal end of the side branch 432 to couple the side branch with another device, such as a source of fluid. The fluid from the source of fluid can be directed into the side branch 432 and thereafter into a lumen in the elongate body 416. Such fluid can be used to reduce the force needed to provide relative motion between the elongate body 84 and the elongate body 416. The lumen within the side branch 432 can have a pressure sensing function. For example, the side branch 432 can be in fluid communication with a pressure sensing device or lumen disposed in the elongate body 416. Such a sensing lumen can be used to track the position of the distal end of the catheter assembly 400.

Figure 6:
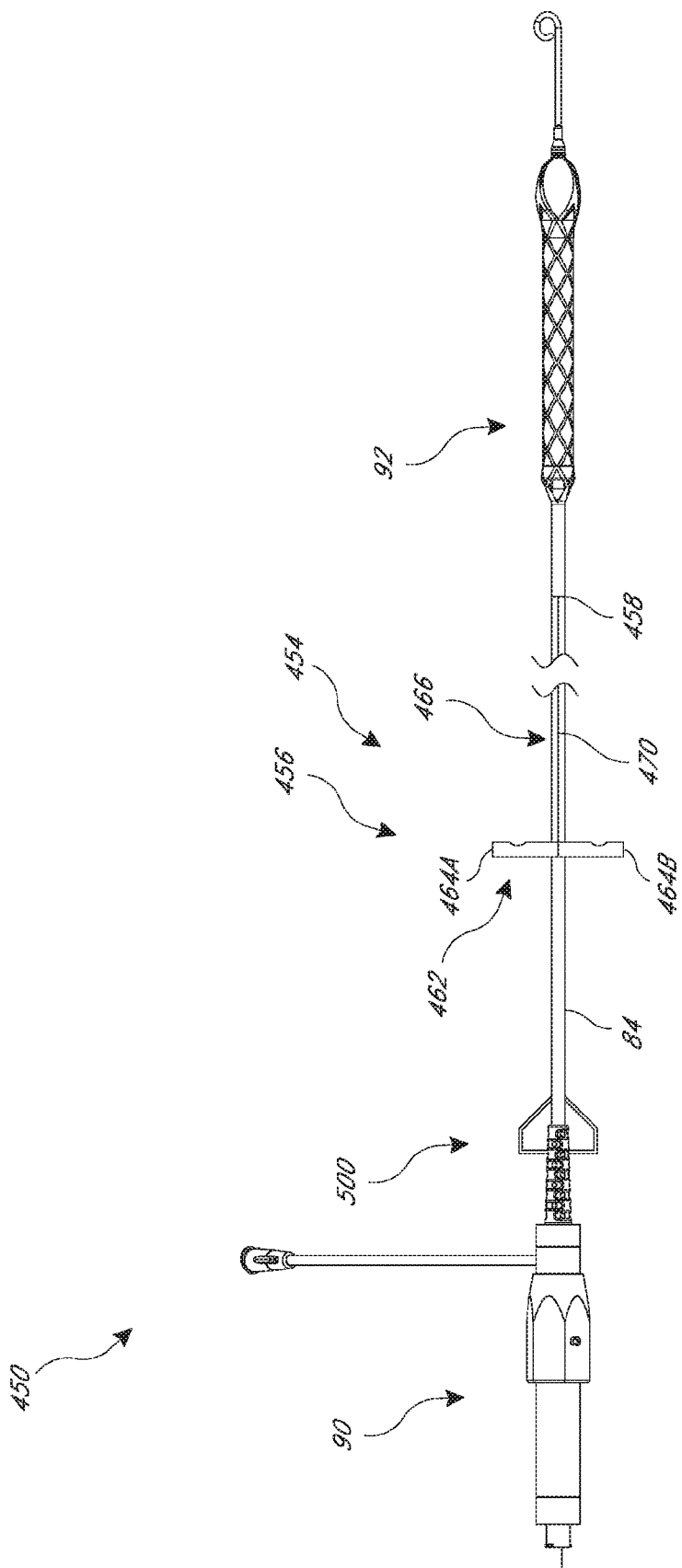
FIG. 6 shows a simplified embodiment of a catheter assembly with a sheath that can be removed from the vasculature of a patient while the working end of the pump is in operation.

FIG. 6 shows a simplified embodiment of a catheter assembly 450 with a sheath assembly 454 that can be removed from a patient while the working end of the pump 10 including the catheter assembly 450 is in operation. The sheath assembly 454 is similar to the sheath assembly 404 except that it includes a low profile hub 456 without a side branch. The hub 456 is disposed at a proximal end 462 opposite a distal end 458. The hub 456 includes two lateral handles 464A, 464B that can be grasped by the clinician to provide relative movement of a body 466 of the sheathe assembly 454 over the elongate body 84. The lateral handles 464A, 464B can also be used to cause the hub 456 to separate into two pieces as discussed further below in connection with Figures and 7A. A separation zone in the hub 456 (e.g., a seam) is disposed immediately proximal of and/or overlaps with a separation zone 470 (e.g., a seam) in the body 466 of the sheath assembly 454. The separation zone 470 can be disposed at one or a plurality of locations about the body 466 and can be composite in nature as discussed above.

FIGS. 7 and 7A convey further details of the sheath assembly 454. FIG. 7 shows two configurations the sheath assembly 454. A first configuration is provided for delivering the catheter assembly 450 into the patient. That is, the body 466 and the hub 456 are intact. A circular inner and outer periphery can provided, at least in the elongate body 466 of the sheath assembly 454. The first configuration is shown by solid lines in the hub 456 and a proximal portion of the body 466. A second configuration is provided, as illustrated by the dashed lines in the hub 456 and the proximal portion of the body 466 in which the handles 464A, 464B are separated from each other. In the second configuration the proximal portion of the elongate body 466 is separated into at least two portions or segments, i.e., a first segment 472A and a second segment 472B. In some methods discuss below the separation shown in FIG. 7 continues to the distal end of the separation zone 470.

FIGS. 7 and 7A illustrate further features. For example, the separation zone 470 can include a first portion 476 and a second portion 480. The first portion 476 is disposed in a proximal portion of the elongate body 466 and the second portion 480 is disposed in a distal portion of the elongate body 466. The proximal portion 476 has a lower resistance to tearing. Accordingly, the proximal portion 476 is configured to resist relatively low radially outward forces or pressures. Such configuration is suitable because the lower portion is not required to retain any compressed structures. As a result, a relatively low force applied to the handles 464A, 464B or to the proximal ends of the segments 472A, 472B causes the handles and/or segments to separate to the second (dashed outer profile) configuration. The distal portion 480 has a higher resistance to tearing. This is advantageous in that the distal portion 480 overlies the expandable cannula 202 and the expandable impeller 300. The impeller and cannula store strain energy when compressed and are continually pressing outwardly on the sheath assemblies 404, 454. Accordingly, by elevating the tear resistance in the distal portion 480, the sheath assembly 454 will not inadvertently or prematurely be force open by the stored strain energy of the cannula 202 and the impeller 300. FIG. 7A shows the packing of these components within the distal portion 480. The impeller 300 is shown schematically somewhat enlarged in the impeller shape but when compressed would be highly deformed and compacted to be disposed within a projection of the body 84 (shown in dashed lines) and also would be disposed within the compressed cannula 202, which would also be compressed to be disposed within the body 84. Because these structures are generally compressed to be contained within a volume having a radius of about one-half or less than the un-compressed radius, high outward forces are applied by these compressed structures on the distal portion of the body of the sheath assembles 404, 454.

FIGS. 7 and 7A show that the separation of the segments 472A, 472B can be facilitated by one or more separation zones, e.g., one or more unitary and/or composite seams. As used in this context a unitary separation zone or same is one that has a uniform resistance to tearing along the length of the separation zone or seam. The separation zones 470A, 470B can be opposed, e.g., on opposite sides of the sheath body 466. The separation zones 470A, 470B can have a composite structure with more resistance to tearing in the distal portion 480 than in the proximal portion 476.

B. Methods of Deployment of Catheter Pump with Removable Outer Sheaths

FIGS. 8-13 illustrate methods of applying catheter systems discussed herein. These images are schematic in order to simplify the illustration but would generally include the components discussed above and illustrated in the figures.

Figure 8:
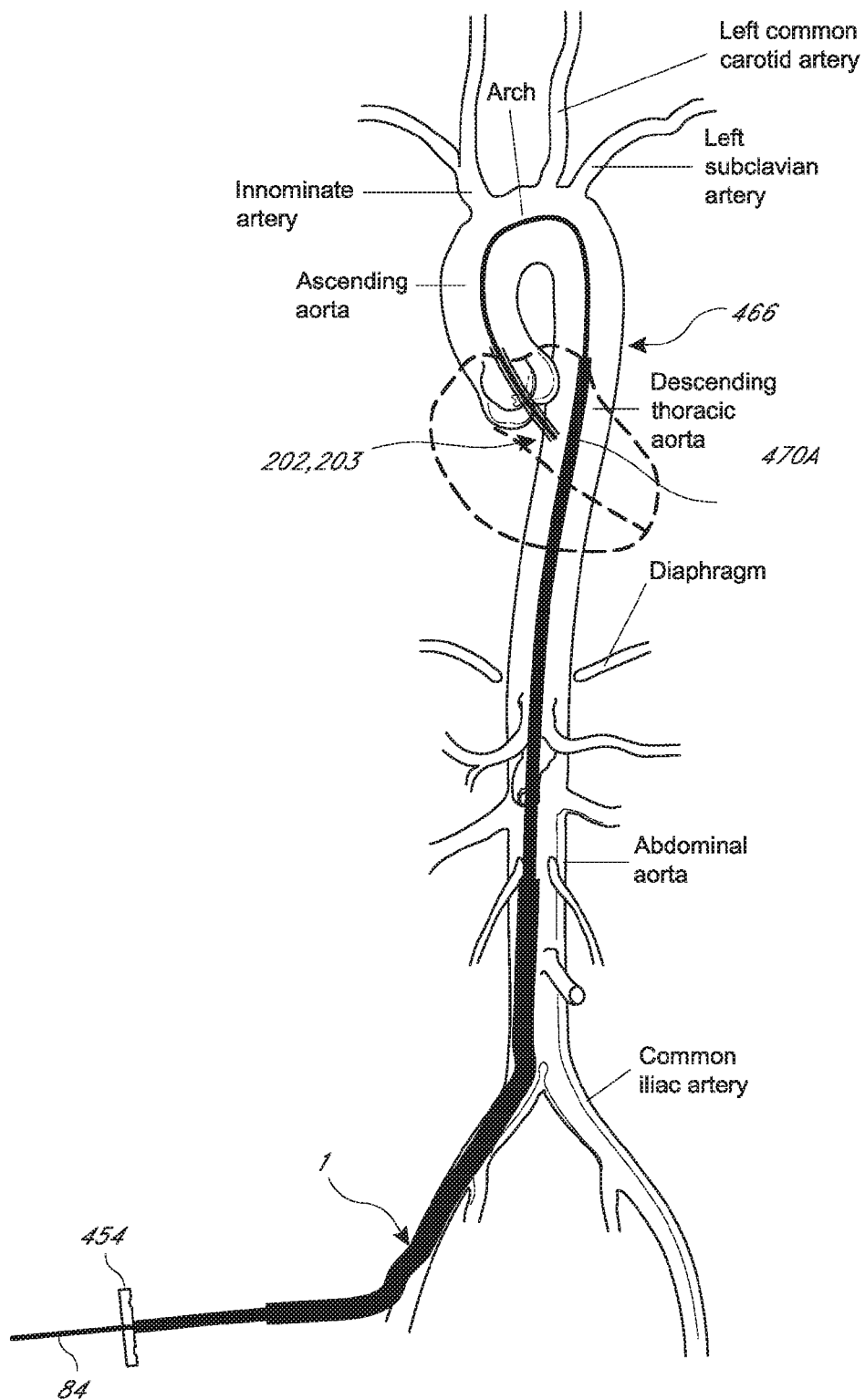
FIGS. 8-13 illustrate methods of using a catheter assembly including a removeable sheath assembly as discussed herein.

FIG. 8 shows a simplified diagram of the vasculature that is traversed in one technique for applying the catheter assembly 450. The catheter assembly 450 is shown in place in one operational configuration. The catheter body 84 which houses a drive cable to cause the impeller 300 to rotate within the cannula 202 is disposed through an introducer sheath I. Between the catheter body 84 and the introducer sheath I is a sheath assembly, for example the sheath assembly 454. The sheath assembly 454 is moveable over the elongate body 84 between a distal position in which the distal end of the body 466 is disposed over the cannula 202 and a proximal position which of the elongate body 466 of the sheath assembly 454 is disposed proximal of the cannula 202. FIG. 8 shows the sheath assembly 454 in the proximal position. A separation zone 470A extends along a length of the body 466 of the sheath assembly 454. In some embodiments the separation zone 470A extends from the proximal end to the distal end of the sheath assembly 454.

Figure 9:
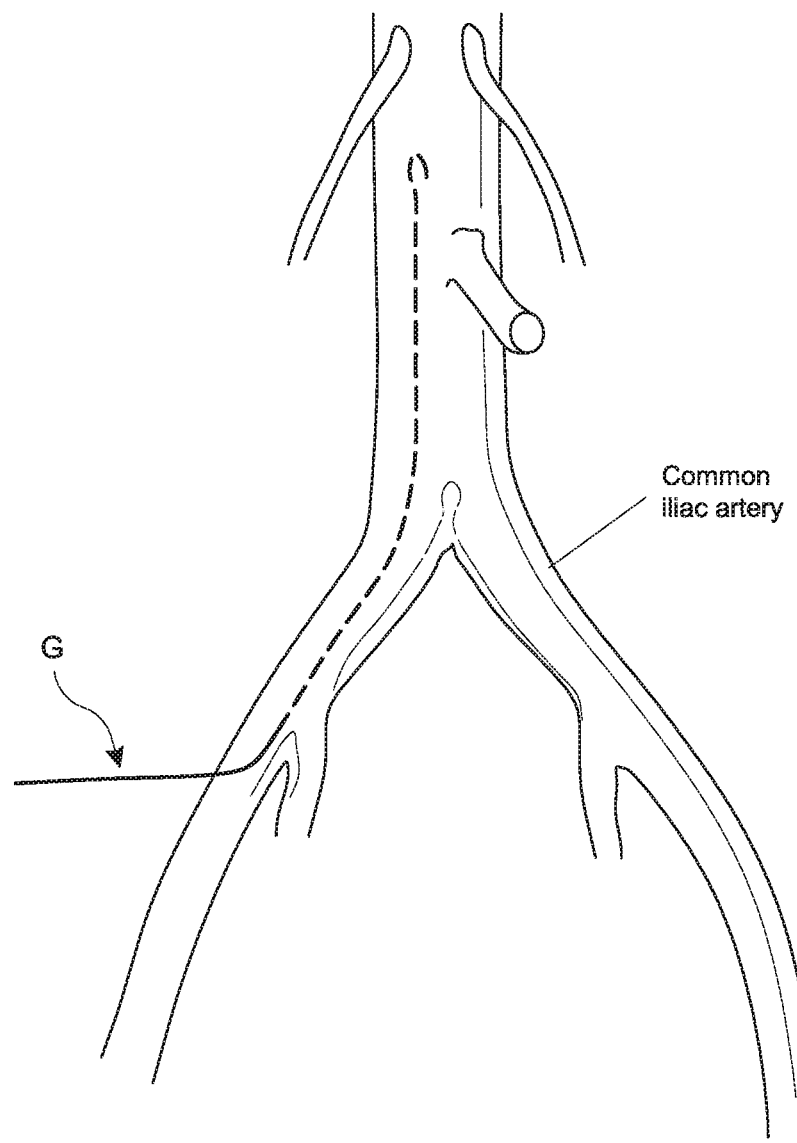
Figure 10:
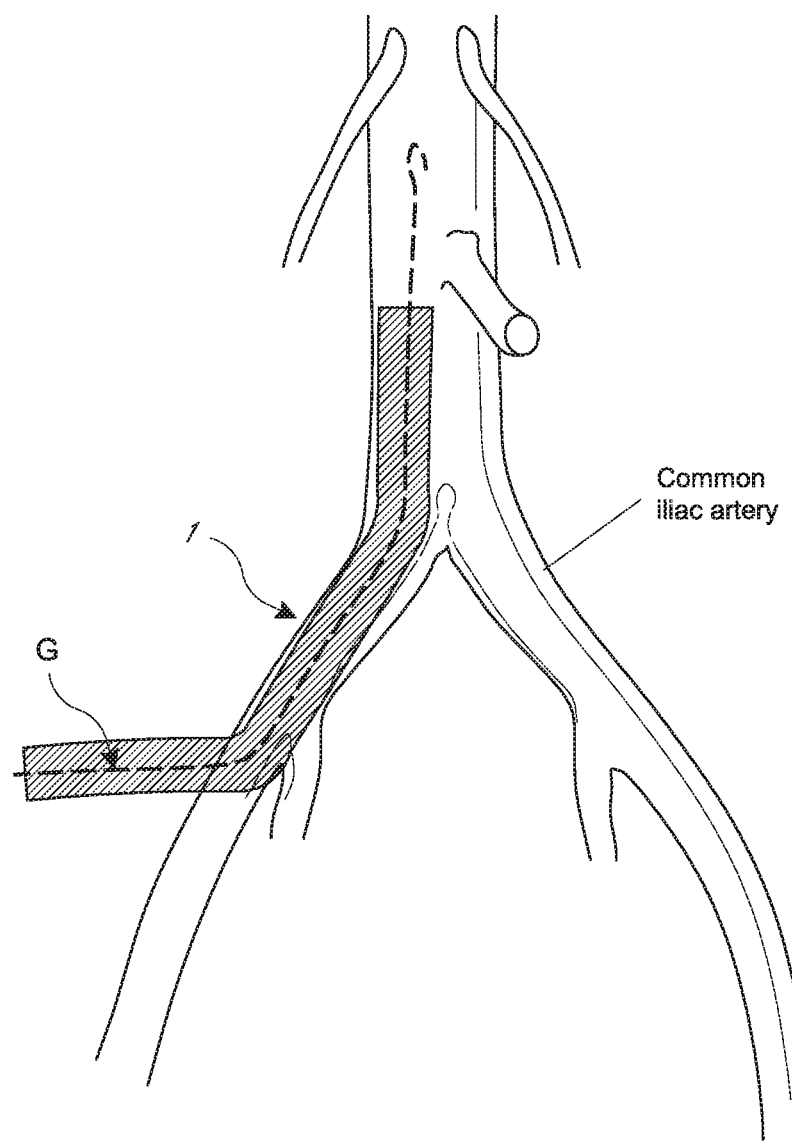

FIGS. 9-12 illustrates steps that enable the catheter assembly 450 to be positioned as shown in FIG. 8. FIG. 9 shows that a guidewire G is placed through a small incision or a needle or other small cannula (not shown) into a peripheral vessel. The guidewire G is advanced from the peripheral access site toward the heart. The peripheral access site is generally the femoral artery, though other vessels could be used as discussed above. For example, on the venous side, the femoral vein or the internal jugular vein could be accessed for supporting the right side of the heart. FIG. 10 shows that the guidewire G provides an access tool for inserting an introducer sheath I that provides a window into the vasculature large enough to deliver the catheter assembly 450 (or variants including the other catheter assemblies described herein). FIG. 10 is exaggerated to show that the introducer sheath I can provide significant obstruction of the blood vessel in which access is provided and also downstream of such vessels and locations.

Figure 11:
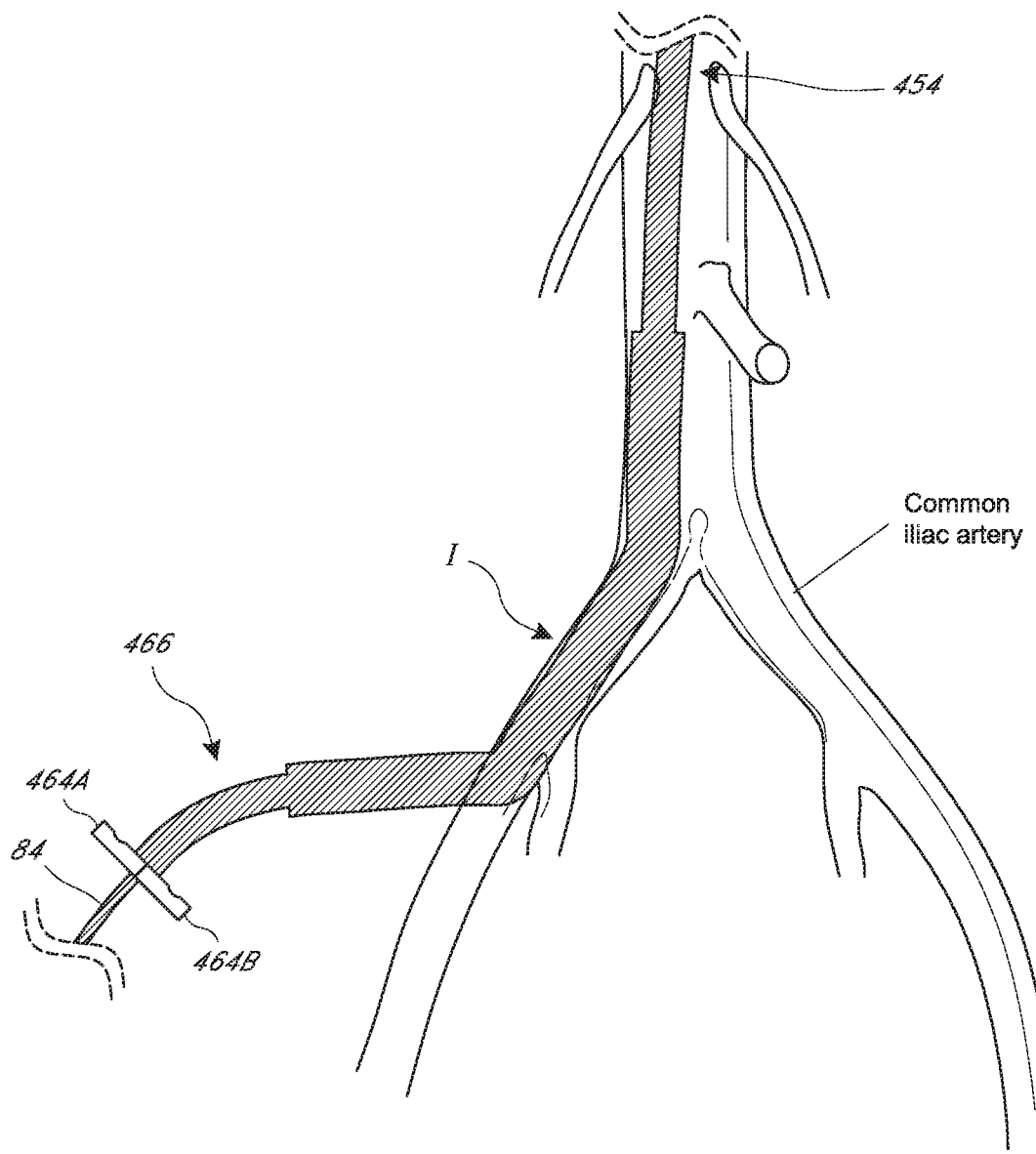

FIG. 11 shows the introduction of the catheter assembly 450 into the vasculature through the introducer I. The catheter assembly 450 generally extends proximally and distally of the illustration as indicated by the break lines. In the distal direction, the catheter assembly 450 is advanced up the descending aorta to ultimately be positioned in the heart, as in FIGS. 4 and 8. An intermediate portion of the catheter assembly 450 including an intermediate portion of the sheath assembly 454 extends through the abdominal aorta (as shown) and into the thoracic aorta (not shown). In these positions the body 466 of the sheath assembly 454 also provides some obstruction to blood flow in the vasculature.

The impeller 300 and the cannula 202 are deployed by providing relative motion between these components and a distal end of the body 466 of the sheath assembly 454. Once the distal end of the body of the sheath assembly 454 is disposed proximally of the proximal end of the cannula 202 the cannula and the impeller 300 will have been permitted to expand. As this point, the sheath assembly 454 provides no role in the operation of the pump 10 and can be removed.

Removal of the sheath assembly 454 can be as illustrated and described in connection with FIGS. 7 and 7A. For example, the handles 464A, 464B which are disposed outside the body of the sheath assembly 454 can be pulled apart which commences the separation of the segments of the sheath assembly 454. Pulling the handles 464A, 464B apart can be accomplished by applying a force transverse to the longitudinal axis of the body 466. In certain embodiments one or more fins 500 (see FIG. 2) can be provided to aid in separating the handles 464A, 464B and/or to propagate a gap in the separation zone or zones 470A, 470B. The fins 500 can be used in a system where one or both of a proximal hub or elongate body of a sheath are not pre-formed with a seam or other structure to reduce the tear force of the sheath. Thus, a catheter system can be configured to segment a sheath assembly even if the sheath assembly is not specifically adapted to tear along a pre-formed zone. FIGS. 5 and 6 show embodiments of the sheath assembly positioned 90 degrees from the position in which the fins 500 would engage the separation zone or zones. In other words, a 90 degree relative rotation of the sheath assembly 90 relative to the elongate body 84 would align the fins 500 with the separation zones 470, 470A, 470B. The fins 500 would play a role in initially separating the handles 464A, 464B by pulling the proximal face of the handles 464A, 464B into contact with the fins 500 until the handles 464A, 464B separate from each other. The fins would then further slide in the separation zone form a gap therein. The body 84 of the catheter assembly 450 can be held in position while the handles 464A, 464B are withdrawn and pulled laterally to further separate the body 466 of the sheath assembly 454.

Figure 12:
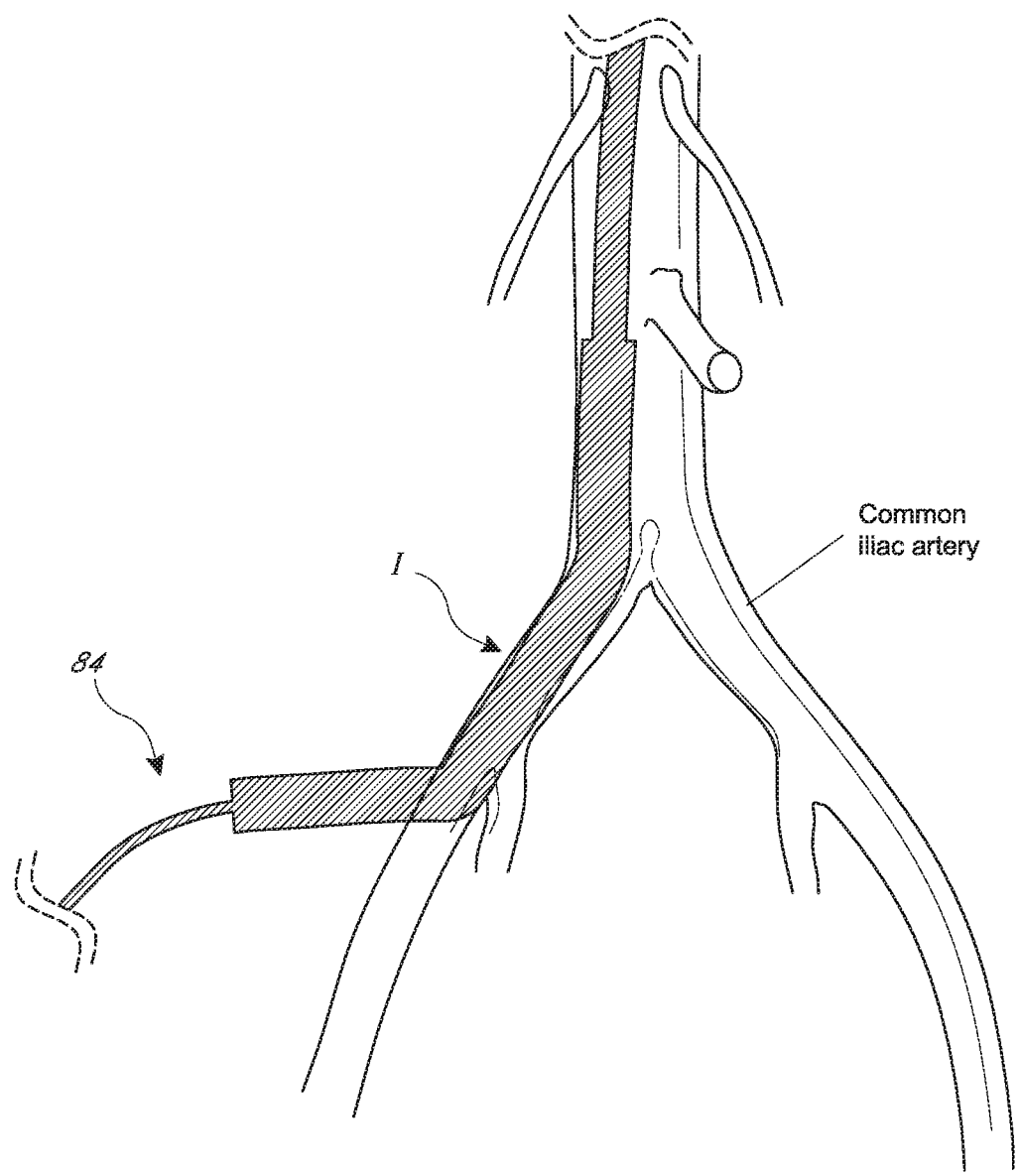

FIG. 12 shows a proximal portion of the body 84 of the catheter assembly 450 extending out of the proximal end of the introducer I and distal portion of the body 84 exposed in the abdominal aorta distal of the distal end of the introducer I. This configuration eliminates the thickness of the body 466 of the sheath assembly 454 between the distal end of the introducer I and the distal end of the position of the body 466 as illustrated in FIG. 8. Eliminating this layer increases the space available for blood flow by at least about 5% and in some cases between about 5% and about 15%. In other embodiments, eliminating the body 466 increases the space available for flow by at least about 15% and in some cases between about 15% and about 20%. Eliminating the body 466 decreases the degree of stretch of the tissues at the puncture site to reduce the likelihood of tearing and/or to eliminate the need for surgical cutdown at the skin or blood vessel access site. In addition, the distal face of the sheath assembly 454 can generate flow disturbances, can be an origin for thrombosis formation and can be lodged on plaque when advanced or, if not operated properly, interfere with the aortic valve leaflets when advanced to collapse the cannula 202 and impeller 300. Thus, eliminating the sheath assembly 454 after the cannula 202 is expanded and during operation of the impeller 300 can improve the overall performance of the pump 10.

Figure 13:
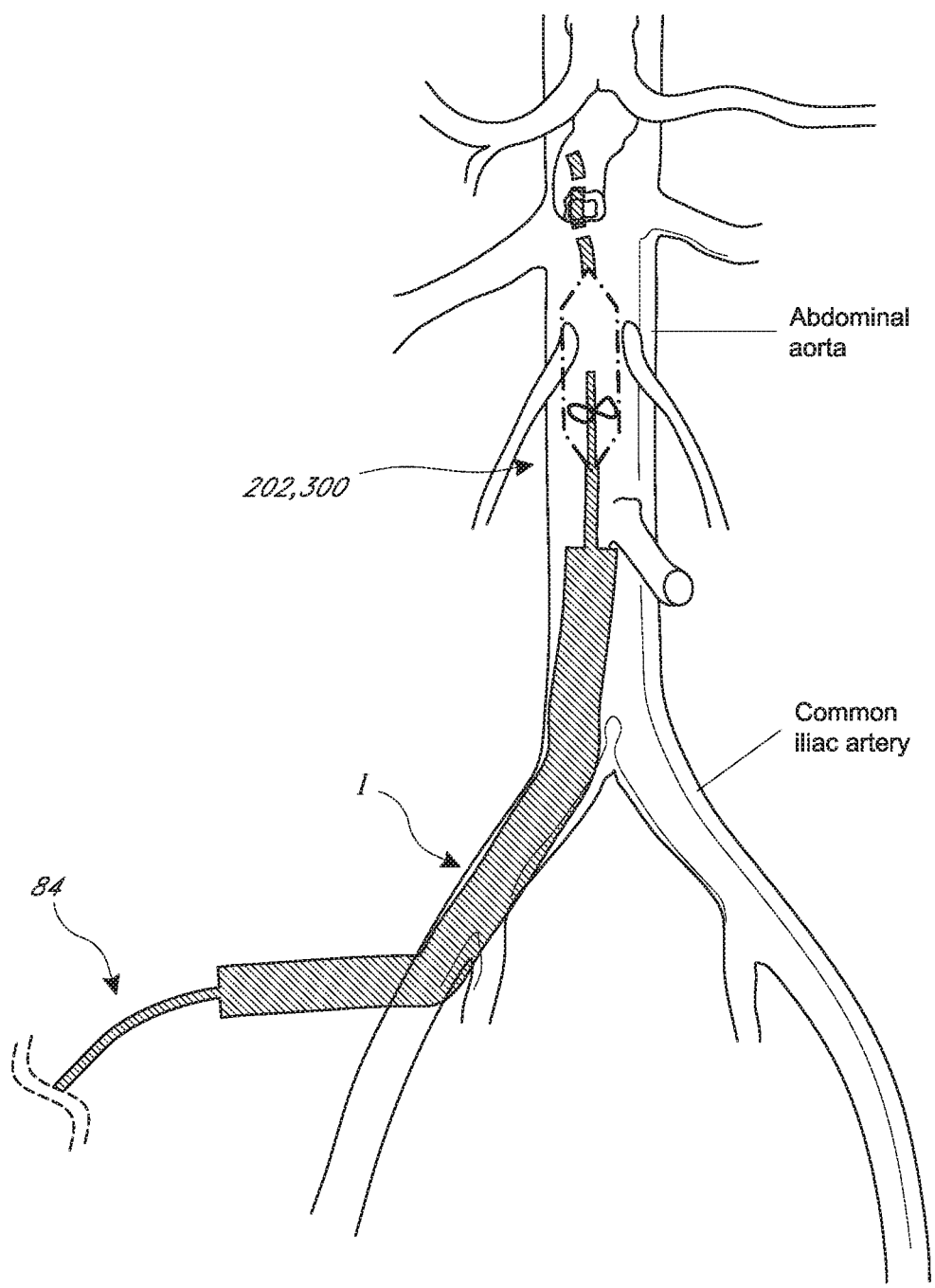

FIG. 13 illustrates a technique for collapsing the cannula 202 and impeller 300 to remove them from the patient. In particular, after the pump 10 is halted and no longer operating to pump blood, the impeller 300 is stationary in the cannula 202. The body 84 of the catheter assembly 450 can be retracted from outside the patient That is a pulling force is applied to the proximal end of the body 84 to provide movement of the body 84 relative to the introducer I such that a distal portion of the body 84 is pulled across the aortic valve and out of the heart. The cannula 202 and impeller 300 are flexible and compressible and thus are atraumatic to the valve leaflets. Further retraction of the body 84 pulls the distal end of the body 84 and cannula 202 with impeller 300 disposed therein along the ascending aorta, over the aortic arch and down the descending aorta. Further retraction of the body 84 pulls the proximal end of the cannula 202 into adjacency with the distal end of the introducer I as illustrated in FIG. 13. The introducer I is configured with sufficient stiffness at the distal end thereof to compress the cannula. Although the introducer I has a bore large than the sheath body 466 so does not require as much compression to initially receive the cannula 202 and impeller 300. In some embodiments, the distal end of introducer I can be shaped to enhance the collapse of the cannula 202. For example, the distal end of the introducer I can comprise shapes and arrangements similar to those illustrated in FIGS. 17A-17D and the associated disclosure of US Patent Publication No. US 2012/0178986, which is incorporated by reference herein in its entirety and for all purposes.

In one variation, the impeller 300 is configured to be retracted into a collapsed position prior to the collapsing of the cannula 202. A drive shaft that is coupled with the impeller 300 can be provided with a mechanism to shift the position of the impeller from a deployed position (as in FIG. 13) to a stored position within an interior space of the body 84 or of a structure coupled with the body 84. Such structures are discussed in more detail in U.S. Pat. No. 7,841,976 and in U.S. Patent Publication 2012/0178986 (also included as an Appendix), both of which are incorporated by reference for further discussion of these features and in their entirety. By shifting the impeller 300 into this stored position the stiffness of the distal portion of the catheter assembly 450 can be greatly reduced. Reduced stiffness of the distal portion of the catheter assembly 450 makes the distal portion of the catheter assembly easier to extract from the patient in a biocompatible manner.

Once the distal portion of the catheter assembly 450 is disposed in the introducer I the introducer I and the distal portion of the catheter assembly 450 can be removed sequentially or together.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter system for a catheter pump, comprising:
an elongate catheter body having a distal portion including an expandable cannula having an inlet and an outlet, the expandable cannula having a delivery profile and an operational profile larger than the delivery profile;
an impeller assembly disposed in the expandable cannula and including an impeller shaft and an impeller body including one or more impeller blades, the impeller blade(s) drawing fluid into the expandable cannula when rotated in the fluid;
a sheath having a cannula retention zone disposed over the expandable cannula and a separation zone, the cannula retention zone having a first configuration adapted to retain the expandable cannula in the delivery profile, the sheath further adapted to be advanced through a vasculature of a patient to deliver the expandable cannula to a target location within the vasculature where it is advanced distally out of the sheath; and
a separation device disposed on the catheter system proximal of the sheath at least when the cannula retention zone of the sheath is disposed over the expandable cannula, wherein, upon advancing the expandable cannula distally out of the sheath, the separation device is adapted to separate the separation zone of the sheath into a first portion and a second portion disposed across a gap, the gap enabling the elongate catheter body to pass between the first and second portion so that the sheath can be removed from the elongate catheter body for operation of the impeller assembly.

2. The catheter system of claim 1, wherein the cannula retention zone comprises a first resistance to tearing, the sheath having an elongate zone proximal of the cannula retention zone and having a second resistance to tearing, the second resistance to tearing being lower than the first resistance to tearing.

3. The catheter system of claim 1, wherein the separation zone includes a composite seam.

4. The catheter system of claim 3, wherein the composite seam includes a first perforated segment disposed in the cannula retention zone and a second perforated segment disposed proximally of the cannula retention zone, the first perforated segment including perforations with less density than in the second perforated segment.

5. The catheter system of claim 1, wherein the separation zone includes a first portion and a second portion opposed to the first portion such that the sheath can be separated into two segments.

6. The catheter system of claim 5 wherein the first and second portions are disposed on opposite sides of the sheath.

7. The catheter system of claim 1, further comprising handles disposed on a proximal end of the sheath, the handles having a first configuration for providing relative motion between the sheath and the elongate catheter body and a second configuration for changing the configuration of the sheath from a tubular configuration to a sheet-like configuration.

8. The catheter system of claim 1, wherein the separation device comprises at least one fin disposed on the elongate catheter body.

9. The catheter system of claim 1, wherein the sheath includes a side branch having a lumen.

10. The catheter system of claim 9, wherein the sheath includes an elongate sheath body comprising a pressure sensing lumen disposed therein and configured to detect fluid pressure at a distal end of the sheath.

11. The catheter system of claim 10, wherein the pressure sensing lumen is coupled in fluid communication with the lumen of the side branch.

12. A method, comprising:
advancing into a vasculature of a patient, to a target location within the vasculature, a catheter assembly including an elongate body, an expandable cannula having an expandable impeller disposed therein, and a sheath having a cannula retention portion disposed over the expandable cannula and the expandable impeller, the cannula retention portion retaining the expandable cannula and the expandable impeller in a low profile configuration;
providing relative motion between the sheath and the expandable cannula to expose the expandable cannula to permit the expandable cannula to expand to a high profile configuration, the high profile configuration having a larger width than the low profile configuration;
pulling a separation zone of the sheath into engagement with a separation device disposed on a proximal portion of the elongate body of the catheter assembly, the elongate body being coupled with the cannula at a distal portion thereof;
separating first and second portions of the sheath along a longitudinal portion thereof to create a gap therealong; and
passing the elongate body through the gap to cause the sheath to be removed from the catheter assembly for operation of the expandable impeller.

13. The method of claim 12, further comprising separating first and second portions of a handle assembly and pulling the first and second portion to extend a gap along the longitudinal direction of the sheath.

14. A method, comprising:
disposing an introducer sheath in a vasculature of a patient;
introducing a catheter assembly into a proximal end of the introducer sheath and into the vasculature through the introducer sheath, the catheter assembly including an elongate body having an expandable cannula coupled with a distal end thereof, the catheter assembly having an expandable impeller being journaled for rotation in the expandable cannula, the catheter assembly further comprising a retainer sheath disposed over the elongate body and the expandable cannula;
advancing the catheter assembly through the vasculature to a source of blood;
advancing the expandable cannula distally relative to and out of the retainer sheath, thereby expanding the expandable impeller for operation in the source of blood;
retracting the retainer sheath proximally into engagement with a separation device disposed on a proximal portion of the elongate body of the catheter assembly and separating the retainer sheath into first and second portions along a longitudinal portion thereof to create a gap therealong through which the catheter assembly passes;
retracting the elongate body into the introducer sheath such that the expandable cannula engages a distal end of the introducer sheath;
providing relative motion between the introducer sheath and the expandable cannula to compress the expandable cannula; and
removing the introducer sheath and the catheter assembly from the patient.

15. The method of claim 14, further comprising prior to retracting the elongate body into the introducer sheath, retracting the impeller into the elongate body of the catheter assembly to compress the impeller.

16. The method of claim 14, further retracting a retainer disposed over the expandable cannula and expandable impeller after introducing the catheter assembly to expand the expandable impeller.

17. The method of claim 16, wherein the retainer sheath comprises a separation zone disposed longitudinally therealong, wherein the separation zone is separable into the first and second portions to create the gap through which the catheter assembly passes.

18. The method of claim 14 further comprising removing the first and second portions of the retainer sheath from the catheter assembly for operation of the expandable impeller to generate a flow of blood.

* * * * *